US011154274B2

(12) United States Patent
Wegner et al.

(10) Patent No.: US 11,154,274 B2
(45) Date of Patent: Oct. 26, 2021

(54) SEMI-RIGID ACOUSTIC COUPLING ARTICLES FOR ULTRASOUND DIAGNOSTIC AND TREATMENT APPLICATIONS

(71) Applicant: Decision Sciences Medical Company, LLC, Poway, CA (US)

(72) Inventors: Allan Wegner, Del Mar, CA (US); Dustin E. Kruse, Grand Island, NY (US); James J. Hayes, San Diego, CA (US); Zachary Staebler, Poway, CA (US)

(73) Assignee: Decision Sciences Medical Company, LLC, Poway, CA (US)

( * ) Notice: Subject to any disclaimer, the term of this patent is extended or adjusted under 35 U.S.C. 154(b) by 0 days.

(21) Appl. No.: 16/856,326

(22) Filed: Apr. 23, 2020

(65) Prior Publication Data
US 2020/0337674 A1    Oct. 29, 2020

Related U.S. Application Data

(60) Provisional application No. 62/837,716, filed on Apr. 23, 2019.

(51) Int. Cl.
*A61B 8/00*    (2006.01)
*A61K 49/22*    (2006.01)

(52) U.S. Cl.
CPC .......... *A61B 8/4281* (2013.01); *A61B 8/4422* (2013.01); *A61B 8/4494* (2013.01); *A61K 49/226* (2013.01)

(58) Field of Classification Search
None
See application file for complete search history.

(56) References Cited

U.S. PATENT DOCUMENTS

| 4,105,018 A | 8/1978 | Greenleaf et al. |
| 4,110,755 A | 8/1978 | Zottl |

(Continued)

FOREIGN PATENT DOCUMENTS

| CA | 2427186 A1 | 5/2001 |
| CA | 2852801 A1 | 5/2013 |

(Continued)

OTHER PUBLICATIONS

Australian Exam Report dated Nov. 1, 2019 for Australian Application No. 2016233279, filed on Mar. 16, 2016 (3 pages).

(Continued)

*Primary Examiner* — Katherine L Fernandez
(74) *Attorney, Agent, or Firm* — Perkins Coie LLP

(57) ABSTRACT

Disclosed are articles, devices and systems providing a semi-rigid acoustic coupling medium for ultrasound diagnostic and treatment techniques. In some aspects, an acoustic coupling article includes a semi-rigid acoustic coupling medium (SACM) able to conform to a receiving body through deformation of the SACM body in order to propagate an acoustic signal within the SACM to and from the receiving body. In some embodiments, the SACM is configured in a shape having one or more attachment portions located at one end of an acoustic interface portion, such that the acoustic interface portion is operable to contact the receiving body to propagate the acoustic signal and the attachment portions are configured to be secured by an acoustic probe device to transmit and receive the propagated acoustic signal.

13 Claims, 12 Drawing Sheets

(56) References Cited

U.S. PATENT DOCUMENTS

| | | |
|---|---|---|
| 4,159,462 A | 6/1979 | Rocha et al. |
| 4,277,367 A | 7/1981 | Madsen et al. |
| 4,437,468 A | 3/1984 | Sorenson |
| 4,463,608 A | 8/1984 | Takeuchi et al. |
| 4,620,546 A | 11/1986 | Aida et al. |
| 4,821,206 A | 4/1989 | Arora |
| 4,830,015 A | 5/1989 | Okazaki |
| 4,888,746 A | 12/1989 | Wurster et al. |
| 5,039,774 A | 8/1991 | Shikinamie et al. |
| 5,181,513 A | 1/1993 | Touboul et al. |
| 5,241,964 A | 9/1993 | McQuilkin |
| 5,269,309 A | 12/1993 | Fort et al. |
| 5,284,143 A | 2/1994 | Rattner |
| 5,329,944 A | 7/1994 | Fabian et al. |
| 5,394,877 A | 3/1995 | Orr et al. |
| 5,417,218 A | 5/1995 | Spivey et al. |
| 5,445,144 A | 8/1995 | Wodicka et al. |
| 5,465,722 A | 11/1995 | Fort et al. |
| 5,522,878 A | 6/1996 | Montecalvo |
| 5,533,510 A | 7/1996 | Koch, III et al. |
| 5,608,690 A | 3/1997 | Hossack et al. |
| 5,623,928 A | 4/1997 | Wright et al. |
| 5,753,095 A | 5/1998 | Alpenfels et al. |
| 5,793,701 A | 8/1998 | Wright et al. |
| 5,800,356 A | 9/1998 | Criton et al. |
| 5,803,089 A | 9/1998 | Ferre et al. |
| 5,806,518 A | 9/1998 | Mittelstadt |
| 5,829,444 A | 11/1998 | Ferre et al. |
| 5,868,676 A | 2/1999 | McCabe et al. |
| 5,873,830 A | 2/1999 | Hossack et al. |
| 5,882,557 A | 3/1999 | Hayakawa et al. |
| 5,902,244 A | 5/1999 | Kobayashi et al. |
| 5,913,823 A | 6/1999 | Hedberg et al. |
| 5,967,980 A | 10/1999 | Ferre et al. |
| 6,016,285 A | 1/2000 | Wright et al. |
| 6,039,694 A | 3/2000 | Larson |
| 6,045,507 A | 4/2000 | Muzilla et al. |
| 6,050,945 A | 4/2000 | Peterson et al. |
| 6,083,164 A | 7/2000 | Oppelt et al. |
| 6,106,464 A | 8/2000 | Bass et al. |
| 6,107,365 A | 8/2000 | Bertozzi et al. |
| 6,110,114 A | 8/2000 | Nock et al. |
| 6,113,544 A | 9/2000 | Mo |
| 6,123,669 A | 9/2000 | Kanda |
| 6,132,375 A | 10/2000 | Napolitano |
| 6,157,592 A | 12/2000 | Kriz et al. |
| 6,205,411 B1 | 3/2001 | DiGioia, III et al. |
| 6,231,834 B1 | 5/2001 | Unger et al. |
| 6,241,676 B1 | 6/2001 | Savord |
| 6,322,567 B1 | 11/2001 | Mittelstadt et al. |
| 6,338,765 B1 | 1/2002 | Statnikov |
| 6,340,363 B1 | 1/2002 | Bolger et al. |
| 6,341,231 B1 | 1/2002 | Ferre et al. |
| 6,402,707 B1 | 6/2002 | Ernst |
| 6,436,045 B1 | 8/2002 | Rafter et al. |
| 6,445,943 B1 | 9/2002 | Ferre et al. |
| 6,508,766 B2 | 1/2003 | Sato et al. |
| 6,537,216 B1 | 3/2003 | Shifrin |
| 6,583,392 B2 | 6/2003 | Hershey et al. |
| 6,585,648 B1 | 7/2003 | Robinson |
| 6,620,101 B2 | 9/2003 | Azzam et al. |
| 6,626,916 B1 | 9/2003 | Yeung et al. |
| 6,652,461 B1 | 11/2003 | Levkovitz et al. |
| 6,687,531 B1 | 2/2004 | Ferre et al. |
| 6,725,082 B2 | 4/2004 | Sati et al. |
| 6,736,780 B2 | 5/2004 | Song et al. |
| 6,757,582 B2 | 6/2004 | Brisson et al. |
| 6,785,571 B2 | 8/2004 | Glossop |
| 6,786,097 B2 | 9/2004 | Song et al. |
| 6,796,988 B2 | 9/2004 | Melkent et al. |
| 6,808,494 B2 | 10/2004 | Shifrin |
| 6,843,957 B2 | 1/2005 | Statnikov |
| 6,918,877 B2 | 7/2005 | Hossack et al. |
| 6,934,575 B2 | 8/2005 | Ferre et al. |
| 6,939,300 B2 | 9/2005 | Petersen et al. |
| 6,960,173 B2 | 11/2005 | Babaev |
| 7,004,906 B1 | 2/2006 | Guracar et al. |
| 7,066,886 B2 | 6/2006 | Song et al. |
| 7,207,939 B2 | 4/2007 | Husher |
| 7,226,456 B2 | 6/2007 | O'Neil et al. |
| 7,291,119 B1 | 11/2007 | de Guise et al. |
| 7,344,609 B2 | 3/2008 | Statnikov |
| 7,395,181 B2 | 7/2008 | Foxlin |
| 7,473,250 B2 | 1/2009 | Makin et al. |
| 7,532,201 B2 | 5/2009 | Quistgaard et al. |
| 7,542,790 B2 | 6/2009 | Jensen et al. |
| 7,566,304 B2 | 7/2009 | Nakamura et al. |
| 7,678,049 B2 | 3/2010 | Tsoref et al. |
| 7,719,515 B2 | 5/2010 | Fujiwara et al. |
| 7,719,689 B2 | 5/2010 | Lee et al. |
| 7,728,487 B2 | 6/2010 | Adachi et al. |
| 7,763,035 B2 | 7/2010 | Melkent et al. |
| 7,798,585 B2 | 9/2010 | Oguri |
| 7,806,823 B2 | 10/2010 | Sakai et al. |
| 7,826,889 B2 | 11/2010 | David et al. |
| 7,835,778 B2 | 11/2010 | Foley et al. |
| 7,835,784 B2 | 11/2010 | Mire et al. |
| 7,837,625 B2 | 11/2010 | Abe |
| 7,905,836 B2 | 3/2011 | Dan |
| 7,917,317 B2 | 3/2011 | McKeon |
| 7,938,777 B2 | 5/2011 | Amiot et al. |
| 7,938,778 B2 | 5/2011 | Sakai |
| 7,982,362 B2 | 7/2011 | Adachi et al. |
| 8,002,705 B1 | 8/2011 | Napolitano et al. |
| 8,038,616 B2 | 10/2011 | Angelsen et al. |
| 8,043,220 B2 | 10/2011 | Okada et al. |
| 8,103,461 B2 | 1/2012 | Glaser et al. |
| 8,105,339 B2 | 1/2012 | Melkent et al. |
| 8,126,533 B2 | 2/2012 | Lavallee |
| 8,147,409 B2 | 4/2012 | Shifrin |
| 8,152,726 B2 | 4/2012 | Amiot et al. |
| 8,165,658 B2 | 4/2012 | Waynik et al. |
| 8,241,217 B2 | 8/2012 | Chiang et al. |
| 8,251,908 B2 | 8/2012 | Vortman et al. |
| 8,253,578 B2 | 8/2012 | Watabe et al. |
| 8,311,611 B2 | 11/2012 | Csavoy et al. |
| 8,323,200 B2 | 12/2012 | Kunita |
| 8,372,070 B2 | 2/2013 | Tanaka et al. |
| 8,374,674 B2 | 2/2013 | Gertner |
| 8,409,099 B2 | 4/2013 | Vitek et al. |
| 8,409,103 B2 | 4/2013 | Grunwald et al. |
| 8,444,564 B2 | 5/2013 | Mahfouz et al. |
| 8,447,388 B2 | 5/2013 | Igarashi |
| 8,491,476 B2 | 7/2013 | Iwama et al. |
| 8,556,834 B2 | 10/2013 | Gertner |
| 8,565,860 B2 | 10/2013 | Kimchy et al. |
| 8,626,267 B2 | 1/2014 | Lavallee |
| 8,675,939 B2 | 3/2014 | Moctezuma de la Barrera |
| 8,771,188 B2 | 7/2014 | Schers et al. |
| 8,774,900 B2 | 7/2014 | Buly et al. |
| 8,814,810 B2 | 8/2014 | Roche et al. |
| 8,864,686 B2 | 10/2014 | Roche et al. |
| 8,880,152 B2 | 11/2014 | Lavallee |
| 8,909,325 B2 | 12/2014 | Kimchy et al. |
| 8,939,909 B2 | 1/2015 | Wegner |
| 9,060,794 B2 | 6/2015 | Kang et al. |
| 9,101,394 B2 | 8/2015 | Arata et al. |
| 9,174,065 B2 | 11/2015 | Gertner |
| 9,196,046 B2 | 11/2015 | Meyer |
| 9,220,571 B2 | 12/2015 | Lavallee |
| 9,244,169 B2 | 1/2016 | Fan et al. |
| 9,248,001 B2 | 2/2016 | Colombet et al. |
| 9,352,171 B2 | 5/2016 | Gertner |
| 9,387,276 B2 | 7/2016 | Sun et al. |
| 9,420,999 B2 | 8/2016 | Wegner |
| 9,572,548 B2 | 2/2017 | Moctezuma de la Barrera |
| 9,597,058 B2 | 3/2017 | Kanayama et al. |
| 9,844,359 B2 | 12/2017 | Gerbaulet et al. |
| 9,872,667 B2 | 1/2018 | Wegner |
| 10,085,722 B2 | 10/2018 | Wegner |
| 10,321,889 B2 | 6/2019 | Wegner |
| 10,426,429 B2 | 10/2019 | Kruse et al. |
| 2002/0068871 A1 | 6/2002 | Mendlein et al. |
| 2002/0099290 A1 | 7/2002 | Haddad |

(56) References Cited

U.S. PATENT DOCUMENTS

| | | |
|---|---|---|
| 2002/0122536 A1 | 9/2002 | Kerrien et al. |
| 2002/0188229 A1 | 12/2002 | Ryaby et al. |
| 2003/0036702 A1 | 2/2003 | Davidsen |
| 2003/0125628 A1 | 7/2003 | Song et al. |
| 2003/0233045 A1 | 12/2003 | Vaezy |
| 2004/0066708 A1 | 4/2004 | Ogawa |
| 2004/0236223 A1 | 11/2004 | Barnes et al. |
| 2005/0101861 A1 | 5/2005 | Satoh |
| 2005/0101867 A1 | 5/2005 | Johnson et al. |
| 2005/0203399 A1 | 9/2005 | Vaezy |
| 2005/0215893 A1 | 9/2005 | Barnes et al. |
| 2006/0004290 A1 | 1/2006 | Smith et al. |
| 2006/0119223 A1 | 6/2006 | Ossman |
| 2006/0173305 A1 | 8/2006 | Asafusa et al. |
| 2007/0066897 A1 | 3/2007 | Sekins et al. |
| 2007/0156050 A1 | 7/2007 | Barnes et al. |
| 2007/0226976 A1 | 10/2007 | Zipparo et al. |
| 2007/0239001 A1 | 10/2007 | Mehi et al. |
| 2007/0239002 A1 | 10/2007 | Alam |
| 2007/0265690 A1 | 11/2007 | Lichtenstein et al. |
| 2007/0276238 A1 | 11/2007 | Sudol |
| 2008/0110263 A1 | 5/2008 | Klessel et al. |
| 2008/0119737 A1 | 5/2008 | Urbano et al. |
| 2008/0200810 A1 | 8/2008 | Buchalter |
| 2008/0208055 A1 | 8/2008 | Bertram et al. |
| 2008/0281202 A1 | 11/2008 | Fraser et al. |
| 2008/0281237 A1 | 11/2008 | Slayton et al. |
| 2009/0043206 A1 | 2/2009 | Towfiq et al. |
| 2009/0093737 A1 | 4/2009 | Gerbaulet et al. |
| 2009/0124871 A1 | 5/2009 | Arshak et al. |
| 2009/0306497 A1 | 12/2009 | Manzke et al. |
| 2010/0029789 A1 | 2/2010 | Chen |
| 2010/0179425 A1 | 7/2010 | Zadicario |
| 2010/0204577 A1 | 8/2010 | Sekins et al. |
| 2010/0268072 A1 | 10/2010 | Hall et al. |
| 2010/0274139 A1 | 10/2010 | Fukukita et al. |
| 2010/0280379 A1 | 11/2010 | Satoh |
| 2010/0286518 A1 | 11/2010 | Lee et al. |
| 2010/0286527 A1 | 11/2010 | Cannon |
| 2011/0092862 A1 | 4/2011 | Chivers |
| 2011/0264012 A1 | 10/2011 | Lautzenhiser et al. |
| 2012/0029345 A1 | 2/2012 | Mahfouz et al. |
| 2012/0238875 A1 | 9/2012 | Savitsky et al. |
| 2012/0253071 A1 | 10/2012 | Rau et al. |
| 2012/0281507 A1 | 11/2012 | Rikoski |
| 2013/0060121 A1 | 3/2013 | Patwardhan et al. |
| 2013/0102875 A1 | 4/2013 | Dogra et al. |
| 2013/0123635 A1 | 5/2013 | Wegner |
| 2013/0144135 A1 | 6/2013 | Mahfouz et al. |
| 2013/0144166 A1 | 6/2013 | Specht et al. |
| 2013/0150863 A1 | 6/2013 | Baumgartner |
| 2013/0165005 A1 | 6/2013 | Berard-Anderson et al. |
| 2013/0218013 A1 | 8/2013 | Barthe et al. |
| 2014/0163377 A1 | 6/2014 | Kang et al. |
| 2014/0180116 A1* | 6/2014 | Lindekugel ............ A61B 8/4455 600/461 |
| 2014/0353248 A1 | 12/2014 | Kuraray |
| 2015/0018682 A1 | 1/2015 | Schers et al. |
| 2015/0038613 A1 | 2/2015 | Sun et al. |
| 2015/0080725 A1 | 3/2015 | Wegner |
| 2015/0088040 A1 | 3/2015 | Barthe et al. |
| 2015/0133788 A1 | 5/2015 | Mauldin, Jr. et al. |
| 2015/0164467 A1 | 6/2015 | Suetoshi et al. |
| 2015/0182191 A1 | 7/2015 | Caluser et al. |
| 2015/0274805 A1* | 10/2015 | Annabi ............ A61L 27/3804 424/93.7 |
| 2015/0313572 A1 | 11/2015 | Gerbaulet et al. |
| 2016/0000409 A1 | 1/2016 | Bruder et al. |
| 2016/0083574 A1* | 3/2016 | Zheng ................ C08L 5/00 522/42 |
| 2016/0100821 A1 | 4/2016 | Eggers et al. |
| 2016/0176128 A1 | 6/2016 | Zhao et al. |
| 2016/0242736 A1* | 8/2016 | Freiburg ............ A61B 17/2251 |
| 2016/0270763 A1 | 9/2016 | Hayes et al. |
| 2016/0354520 A1 | 12/2016 | Sun et al. |
| 2017/0100092 A1 | 4/2017 | Kruse et al. |
| 2017/0368333 A1* | 12/2017 | Loudin ................ C08F 220/20 |
| 2018/0126677 A1 | 5/2018 | Zhao et al. |
| 2018/0240366 A1* | 8/2018 | Felsinger ............... G09B 23/30 |
| 2018/0244858 A1* | 8/2018 | Illeperuma ............ C08F 220/06 |
| 2019/0167234 A1 | 6/2019 | Wegner |
| 2019/0200957 A1 | 7/2019 | Freiburg et al. |

FOREIGN PATENT DOCUMENTS

| | | |
|---|---|---|
| CN | 100354651 C | 12/2007 |
| CN | 101325913 A | 12/2008 |
| CN | 102258399 B | 11/2012 |
| CN | 104169739 A | 11/2014 |
| EP | 952461 A2 | 10/1999 |
| EP | 1707124 A2 | 4/2006 |
| EP | 1795917 A2 | 6/2007 |
| EP | 1854406 A1 | 11/2007 |
| EP | 1955668 A1 | 8/2008 |
| EP | 2033579 A1 | 3/2009 |
| GB | 2379392 B | 3/2003 |
| GB | 2472066 A | 1/2011 |
| IL | 232148 A | 7/2019 |
| JP | 55051351 A | 4/1980 |
| JP | 58195550 A | 11/1983 |
| JP | 60048736 A | 3/1985 |
| JP | 62117535 A | 5/1987 |
| JP | 8038473 A | 2/1996 |
| JP | 2000041980 A | 2/2000 |
| JP | 2003190157 A | 7/2003 |
| JP | 2004147852 A | 5/2004 |
| JP | 2005152608 A | 6/2005 |
| JP | 2010082425 A | 4/2010 |
| JP | 2011177461 A | 9/2011 |
| JP | 2012002586 A | 1/2012 |
| JP | 2013056156 A | 3/2013 |
| WO | 2002024094 A2 | 3/2002 |
| WO | 2007023477 A2 | 3/2007 |
| WO | 2007069156 A1 | 6/2007 |
| WO | 2009009064 A1 | 1/2009 |
| WO | 2009020617 A1 | 2/2009 |
| WO | 2009063421 A1 | 5/2009 |
| WO | 2013066821 A2 | 5/2013 |
| WO | 2013103956 A1 | 7/2013 |
| WO | 2014128593 A1 | 8/2014 |
| WO | 2014150780 A2 | 9/2014 |
| WO | 2014150961 A1 | 9/2014 |
| WO | 2014186904 A1 | 11/2014 |
| WO | 2015038554 A2 | 3/2015 |
| WO | 2016044830 A1 | 3/2016 |
| WO | 2016138257 A1 | 9/2016 |
| WO | 2016149427 A1 | 9/2016 |
| WO | 2017164902 A1 | 9/2017 |

OTHER PUBLICATIONS

Australian Exam Report dated Oct. 18, 2019 for Australian Application No. 2016222637, filed on Feb. 25, 2016 (3 pages).

Callow, H.J., "Signal Processing for Synthetic Aperture Sonar Image Enhancement," Thesis for Ph.D. in Electrical and Electronic Engineering at the University of Canterbury, Christchurch, New Zealand, 273 pages, Apr. 2003.

Cao, Z. et al., "Fabrication and properties of thermosensitive organic/inorganic hybrid hydrogel thin films," Langmuir, American Chemical Society, vol. 24, No. 10, May 20, 2008, pp. 5543-5551.

Chiao, R., "Coded Excitation for Diagnostic Ultrasound: A System Developer's Perspective," *IEEE Transactions on Ultrasonics, Ferroelectrics, and Frequency Control*, 52(2):160-170, Feb. 2005.

Choe, J.W., et al., "Volumetric real-time imaging using a CMUT ring array," IEEE Transactions on Ultrasonics, Ferroelectrics, and Frequency Control, 59(6):1201-1211, Jun. 2012.

Demi, L., et al., "In Vitro and In Vivo Tissue Harmonic Images Obtained With Parallel Transmit Beamforming by Means of Orthogonal Frequency Division Multiplexing," IEEE Transactions on Ultrasonics, Ferroelectrics, and Frequency Control, 62(1):230-235, Jan. 2015.

(56) References Cited

OTHER PUBLICATIONS

European Search Report dated Apr. 19, 2017 for European Application No. 14844538.0, filed on Sep. 9, 2014 (10 pages).
European Search Report dated Feb. 1, 2019 for European Application No. 16756353.5, filed on Feb. 25, 2016 (14 pages).
European Search Report dated Jun. 29, 2015 for European Application No. 12845256.2, filed on Oct. 29, 2012 (8 pages).
European Search Report dated Nov. 9, 2018 for European Application No. 16765701.4, filed on Mar. 16, 2016 (6 pages).
Extended European Search Report dated Feb. 15, 2019 for European Application No. 16765701.4, filed on Mar. 16, 2016 (14 pages).
Extended European Search Report dated Jul. 2, 2019 for European Application No. 16756353.5, filed on Feb. 25, 2016 (14 pages).
Extended Search Report dated Jun. 18, 2019 for European Application No. 16854507.7, filed on Oct. 7, 2016 (11 pages).
Hunter, A.J., et al., "A Comparison of Fast Factorised Back-Projection and Wavenumber Algorithms for SAS Image Reconstruction," Proceedings of the World Congress on Ultrasonics, 4 pages, (2003).
International Search Report and Written Opinion dated Dec. 29, 2016 for International Application No. PCT/US2016/056159, filed on Oct. 7, 2016 (7 pages).
International Search Report and Written Opinion dated Jul. 6, 2016 for International Application No. PCT/US2016/019554, filed on Feb. 25, 2016 (12 pages).
International Search Report and Written Opinion dated Mar. 3, 2015 for International Application No. PCT/US2014/054855, filed on Sep. 9, 2014 (11 pages).
International Search Report and Written Opinion dated May 15, 2013 for International Application No. PCT/US2012/062435, filed on Oct. 29, 2012 (9 pages).
International Search Report and Written Opinion dated May 18, 2020 for International Application No. PCT/US20/18123, filed on Feb. 13, 2020 (11 pages).
Ito, T., et al., "Evaluation of Acoustic Imaging System Using Correlation Division in Synthetic Transmit Aperture with Multicarrier Signals," IEICE Transactions on Fundamentals of Electronics, Communications and Computer Sciences, E94-A(10):1907-1919, Oct. 2011.
Jensen, J.A., et al., "Synthetic Aperture Ultrasound Imaging," Ultrasonics, 44(Suppl 1):e5-e15, Dec. 2006.
Koch, A., et al., "An Ultasound Tomography System With Polyvinyl Alcohol (PVA) Moldings for Coupling: In Vivo Results for 3-D Pulse-Echo Imaging of the Female Breast," IEEE Transactions on Ultrasonics, Ferroelectrics, and Frequency Control, 62(2):266-279, Feb. 2015.
Kundur, D., et al., "A Novel Blind Deconvolution Scheme for Image Restoration Using Recursive Filtering," IEEE Transactions on Signal Processing, 46(2):375-390, Feb. 1998.
Misaridis, T., "Use of Modulated Excitation Signals in Medical Ultrasound. Part I: Basic Concepts and Expected Benefits," *IEEE Transactions on Ultrasonics, Ferroelectrics, and Frequency Control*, 52(2):177-191, Feb. 2005.
Misaridis, T., "Use of Modulated Excitation Signals in Medical Ultrasound. Part II: Design and Performance for Medical Imaging Applications," *IEEE Transactions on Ultrasonics, Ferroelectrics, and Frequency Control*, 52(2):192-207, Feb. 2005.
Misaridis, T., "Use of Modulated Excitation Signals in Medical Ultrasound. Part III: High Frame Rate Imaging," *IEEE Transactions on Ultrasonics, Ferroelectrics, and Frequency Control*, 52(2):208-219, Feb. 2005.
O'Donnell, M., "Coded Excitation for Synthetic Aperture Ultrasound Imaging," *IEEE Transactions on Ultrasonics, Ferroelectrics, and Frequency Control*, 52(2):171-176, Feb. 2005.
Office Action dated Jun. 4, 2019 for Japanese Application No. 2017-187288, filed on Oct. 29, 2012 (3 pages).
Office Action dated Oct. 29, 2019 for Japanese Application No. 2018-145683, filed on Sep. 9, 2014 (3 pages).
Office Action dated Dec. 4, 2019 for Chinese Application No. 201680023999.9, filed on Feb. 25, 2016 (23 pages).
Office Action dated Jul. 3, 2018 for Japanese Application No. 2017-187288, filed on Oct. 29, 2012 (6 pages).
Office Action dated Sep. 13, 2016 for Japanese Application No. 2014-539114, filed on Oct. 29, 2012 (4 pages).
Office Action dated Sep. 19, 2017 for Japanese Application No. 2016-542050, filed on Sep. 9, 2014 (15 pages).
Office Action dated Sep. 2, 2015 for Chinese Application No. 201280065031.4, filed on Oct. 29, 2012 (26 pages).
Prokop A F et al., "Polyacrylamide gel as an acoustic coupling medium for focused ultrasound therapy." Ultrasound in Medicine and Biol, New York, NY, US, vol. 29, No. 9, Sep. 1, 2003, pp. 1351-1358.
Rui Silva, S., et al., "2 Synthetic Aperture Techniques for Sonar Systems," Advances in Sonar Technology, edited by Sergio Rui Silva, publisher I-Tech Education and Publishing, ISBN 978-3-902613-48-6, pp. 15-42, Feb. 2009.
Singapore Exam Report dated Feb. 26, 2019 for Singapore Application No. 11201706953Y, filed on Feb. 25, 2016 (6 pages).
Singapore Search Report dated Sep. 24, 2018 for Singapore Application No. 11201706953Y, filed on Feb. 25, 2016 (13 pages).
Singapore Written Opinion dated Jul. 10, 2017 for Singapore Application No. 11201601906P, filed on Sep. 9, 2014 (8 pages).
Singapore Written Opinion dated Jun. 21, 2018 for Singapore Application No. 11201707641P, filed on Mar. 16, 2016 (8 pages).
Zhu, S., et al., "SAS Autofocus Based on Phase Gradient Autofocus," IEEE 2011 Fourth International Workshop on Chaos-Fractals Theories and Applications (IWCFTA), pp. 298-301, Oct. 19-22, 2011.
International Search Report and Written Opinion dated Jul. 16, 2020 for International App. PCT/US20/29564 filed Apr. 23, 2020, 11 pages.
International Search Report and Written Opinion dated Jul. 2, 2020 for International Application No. PCT/US2020/021456, filed on Mar. 6, 2020, 16 pages.
Second Office Action dated Jul. 14, 2020 for Chinese Patent Application No. 201680023999.9 (41 pages).
Office Action dated Sep. 23, 2020 in Israel Patent Application No. 254158, 3 pages.

\* cited by examiner

Example of SAC 300 conforming between a receiving body (e.g., breast) and an acoustic transducers of probe 390

Example of SAC 300 conforming between a receiving body (e.g., abdomen) and an acoustic transducers of probe 390

SEMI-RIGID ACOUSTIC COUPLING ARTICLES FOR ULTRASOUND DIAGNOSTIC AND TREATMENT APPLICATIONS

CROSS-REFERENCE TO RELATED APPLICATIONS

This patent document claims priorities to and benefits of U.S. Provisional Patent Application No. 62/837,716 titled "SEMI-RIGID ACOUSTIC COUPLING ARTICLES FOR ULTRASOUND DIAGNOSTIC AND TREATMENT APPLICATIONS" filed on Apr. 23, 2019. The entire content of the aforementioned patent application is incorporated by reference as part of the disclosure of this patent document.

TECHNICAL FIELD

This patent document relates to methods, devices and articles for an acoustic coupling medium useful for ultrasound imaging.

BACKGROUND

Acoustic imaging is an imaging modality that employs the properties of sound waves traveling through a medium to render a visual image. High frequency acoustic imaging has been used as an imaging modality for decades in a variety of biomedical fields to view internal structures and functions of animals and humans. High frequency acoustic waves used in biomedical imaging may operate in different frequencies, e.g., between 1 and 20 MHz, or even higher frequencies, and are often termed ultrasound waves. Some factors, including inadequate spatial resolution and tissue differentiation, can lead to less than desirable image quality using conventional techniques of ultrasound imaging, which can limit its use for many clinical indications or applications.

SUMMARY

Disclosed are articles, devices and systems providing a semi-rigid acoustic coupling medium for ultrasound diagnostic and treatment techniques.

In some aspects, an acoustic coupling article includes a semi-rigid acoustic coupling medium (SACM) operable to conform to a receiving body to propagate an acoustic signal within the SACM to and from the receiving body.

In some aspects, an acoustic coupling article includes a semi-rigid acoustic coupling medium (SACM) operable to contact and conform to an array of transducer elements at a first end of the SACM and to a receiving body at a second end of the SACM to propagate acoustic signals within the SACM between the array of transducer elements and the receiving body. The SACM includes one or more hydrogel materials in a single acoustic coupling article, where the SACM is structured to have one or more attachment portions located at the first end and an acoustic interface portion spanning away from the one or more attachment portions and terminating at the second end, such that an outward surface of the acoustic interface portion at the second end is structured to (i) be substantially flat, at least at a portion of the outward surface, (ii) have a single curve along one direction of the outward surface, at least at a portion of the outward surface, and/or (iii) have multiple curves in multiple directions along the outward surface, at least at a portion of the outward surface. The outward surface is operable to conform to the receiving body for propagation of the acoustic signals into and from the receiving body. The one or more attachment portions are configured to be secured by an acoustic probe device having the array of transducer elements to transmit and receive the propagated acoustic signals.

In some aspects, an acoustic coupling article includes a semi-rigid acoustic coupling medium (SACM) operable to contact and conform to an array of transducer elements at a first end of the SACM and to a receiving body at a second end of the SACM to propagate acoustic signals within the SACM between the array of transducer elements and the receiving body. The SACM includes a single hydrogel material and is structured to have a shape including one or more attachment portions located at the first end and an acoustic interface portion spanning away from the one or more attachment portions and terminating at the second end, such that an outward surface of the acoustic interface portion at the second end is structured to (i) have a single curve along one direction of the outward surface, at least at a portion of the outward surface, and/or (ii) have multiple curves in multiple directions along the outward surface, at least at a portion of the outward surface. The outward surface is operable to conform to the receiving body to propagate the acoustic signals into and from the receiving body. The attachment portions are configured to be secured by an acoustic probe device having the array of transducer elements to transmit and receive the propagated acoustic signals through the single hydrogel material.

In some aspects, an acoustic probe device includes a housing; an array of transducer elements attached to the housing and operable to transmit acoustic signals toward a target volume in a receiving body and received returned acoustic signals that return from at least part of the target volume; and a semi-rigid acoustic coupling medium (SACM) operable to contact and conform to the array of transducer elements at a first end of the SACM and, when the acoustic probe device is engaged with the receiving body, to contact and conform to the receiving body at a second end of the SACM for propagating the transmitted and received returned acoustic signals within the SACM between the array of transducer elements and the receiving body. The SACM includes one or more individual hydrogel materials in a single SACM, where the SACM is structured to have one or more attachment portions located at the first end and an acoustic interface portion spanning away from the one or more attachment portions and terminating at the second end, such that an outward surface of the acoustic interface portion at the second end is structured to (i) be substantially flat, at least at a portion of the outward surface, (ii) have a single curve along one direction of the outward surface, at least at a portion of the outward surface, and/or (iii) have multiple curves in multiple directions along the outward surface, at least at a portion of the outward surface. The outward surface is able to conform to the receiving body for propagation of the acoustic signals into and from the receiving body. The one or more attachment portions are configured to be secured by the acoustic probe device having the array of transducer elements to transmit and receive the propagated acoustic signals. In some implementations, the device is included in an acoustic imaging system configured to produce a synthetic aperture and/or a tomographic image with high resolution of an anatomical structure of a human or non-human subject based on mechanical and acoustic properties of the SACM.

The subject matter described in this patent document can be implemented in specific ways that provide one or more of the following features.

DETAILED DESCRIPTION

Figure 1A:
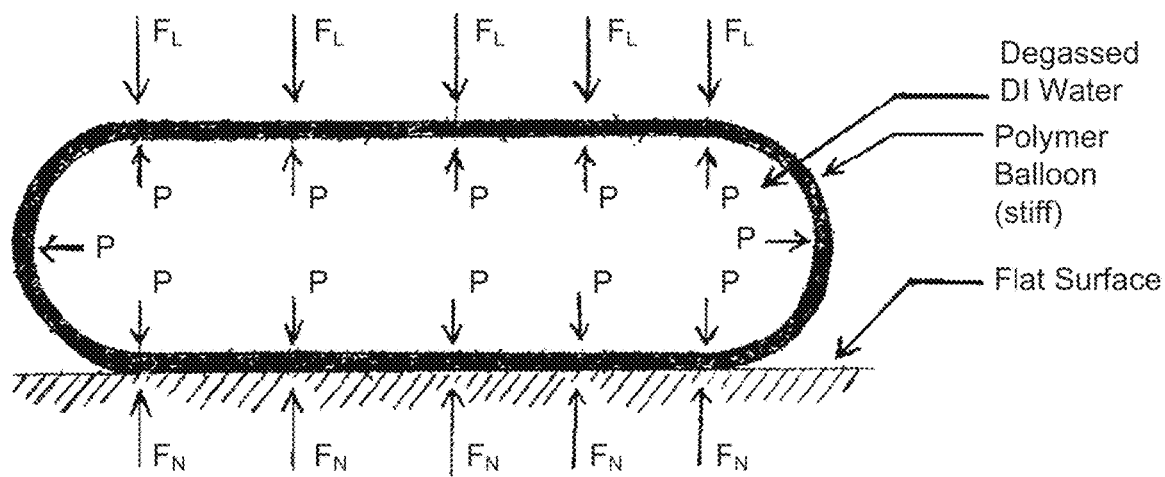
FIGS. 1A and 1B show diagrams illustrating a conventional acoustic couplant which exhibits a lack of conformability to a patient's skin.

Acoustic imaging can be performed by emitting an acoustic waveform (e.g., pulse) within a physical elastic medium, such as a biological medium, including tissue. The acoustic waveform is transmitted from a transducer element (e.g., of an array of transducer elements) toward a target volume of interest (VOI). Propagation of the acoustic waveform in the medium toward the target volume can encounter structures that cause the acoustic waveform to become partly reflected from a boundary between two mediums (e.g., differing biological tissue structures) and partially transmitted. The reflection of the transmitted acoustic waveform can depend on the acoustic impedance difference between the two mediums (e.g., at the interface between two different biological tissue types). For example, some of the acoustic energy of the transmitted acoustic waveform can be scattered back to the transducer at the interface to be received, and processed to extract information, while the remainder may travel on and to the next medium. In some instances, scattering of the reflection may occur as the result of two or more impedances contained in the reflective medium acting as a scattering center. Additionally, for example, the acoustic energy can be refracted, diffracted, delayed, and/or attenuated based on the properties of the medium and/or the nature of the acoustic wave.

Acoustic wave speed and acoustic impedance differences can exist at the interface between the transducer and the medium to receive the acoustic waveform, e.g., referred to as the receiving medium, for propagation of the acoustic waveform toward the target volume, which can disrupt the transmission of the acoustic signal for imaging, range-Doppler measurement, tissue characterization (e.g., Acoustic Radiation Force Impulse—ARFI), or therapeutic applications. Acoustic impedance differences caused due to differing material properties (e.g., material density) of the two mediums and the acoustic wave velocity, such that a substantial amount of the emitted acoustic energy will be reflected at the interface rather than transferred in full across the interface. In typical acoustic (e.g., ultrasound) imaging or therapy applications, for example, a transmission gel is applied to the receiving medium (i.e., the skin of a subject) at the interface where the transducers will make contact to improve the transfer of the acoustic waveform(s) from the transducer to the body and the reception of the returned acoustic waveform(s) from the body back to the transducer. In such applications without the ultrasound gel, the interface may include air as a component of the medium between the receiving medium (e.g., living skin tissue) and the transducer, and an acoustic impedance mismatch in the transducer-to-air and the air-to-body discontinuity causes the scattering (e.g., reflection) of the emitted acoustic energy.

Despite relatively good success in reducing acoustic impedance difference at the interface, when dispensed on the VOI, acoustic transmission gels may contain tiny packets of air that can disrupt the transmission of acoustic signals. Additionally, many patients complain of discomforts with the use of gels dispensed on their skin, e.g., such as temperature, stickiness, or other. More concerning, however, acoustic transmission gels can become contaminated during production or storage, which has led to infections within some patients. For subjects with hair on their skin at the location where the transducer is to be placed, these subjects typically must shave or otherwise remove the external hair which exasperates the trapping of air between the skin and gel.

For non-normal angles of incidence of the acoustic wave relative to the interface, the differences in the acoustic wave speed can result in refraction of the acoustic sound wave. Acoustic wave speed differences at the interface cause the propagation path of longitudinal acoustic waves to refract or change direction according to Snell's Law as a function of the angle of incidence and the acoustic wave speeds either side of the interface. Accumulations of infinitesimal amounts of refraction as the wave propagates in a heterogeneous material results in bending or curvature in the path of the acoustic wave.

As conventional ultrasound (US) imaging assumes that acoustic waves travel in straight lines, refraction along the acoustic path causes degradation and distortion in the resulting image due the ambiguity it creates for the arrival time and location of an acoustic waveform in space for both transmission and reception. A material that matches the acoustic wave speed at the interface significantly reduces the effects of refraction, resulting in a clearer and less ambiguous image. Additionally, a semi-rigid material that has a homogeneous acoustic wave speed throughout will minimize the potential for curvature of acoustic wave paths inside the material.

Ultrasound imaging gained interest in the medical imaging community for portability, multiple anatomic target modalities, safety, and relatively low cost when compared to X-ray, computerized tomography (CT), and magnetic resonance imaging (MRI) techniques. Some modalities focus entirely on cardiology and can create 4-D images of beating ventricles. Other modalities are dedicated calculators that compute fluid flow through tiny corpuscular capillaries in the liver and spleen whereas other modalities simply use the US as a general-purpose machine. Regardless how narrow or broad the application, all US machines suffer from the same limitations engendered from traditional ultrasound design, i.e., loss of image quality at depth and low near field resolution. While the image depth depends mostly on array design and transducer frequency, the obfuscated near field is the result of large impedance mismatch differences between the transducer interface and patient interface and the focal point of the transducer.

Near field convolution is also a problem encountered in many clinical, US diagnostic techniques, especially for synovial joints which are bundles of tendon, fluid, bone, and muscle tightly bound together under a thin, sinewy veil of skin and tissue. This is a ubiquitous problem, and many clinicians have resorted to filling a rubber glove with tap water to act as a portable, quasi-water bath that doubled as a standoff, e.g., any acoustic coupling material providing distance between the transducer interface and patient interface. Simple, cost effective, and fast to implement, this artifice was a solution, albeit inadequate, for generating quick non-visceral US images with linear arrays.

Figure 1B:
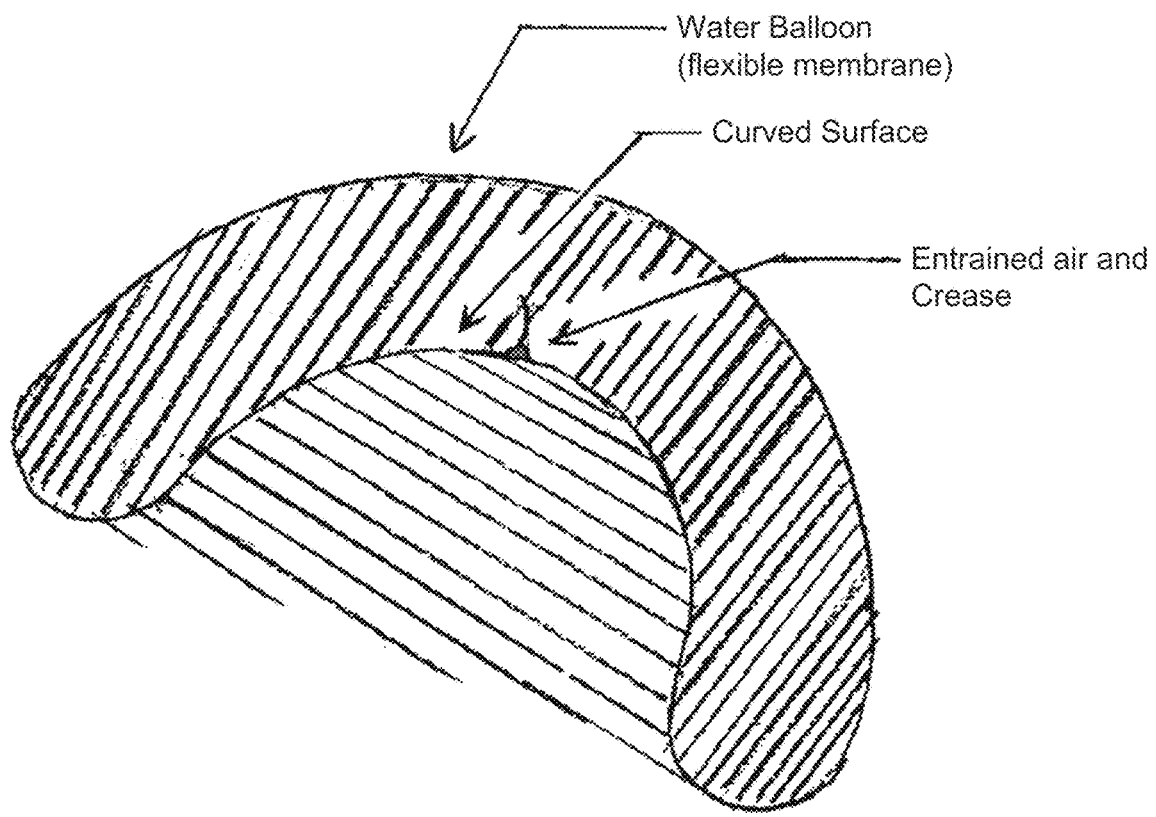
Figure 2:
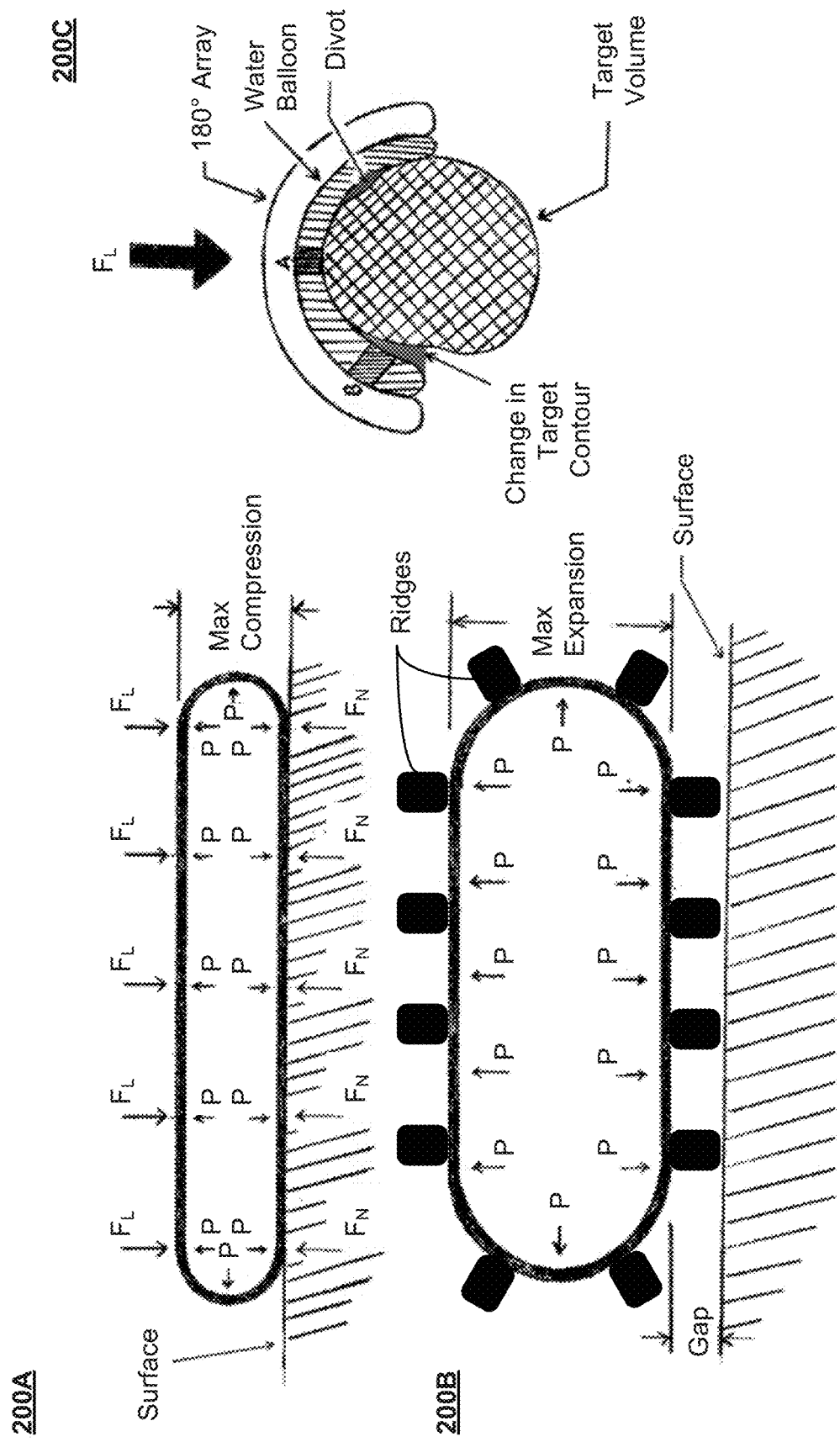
FIG. 2 shows diagrams illustrating conventional acoustic couplants, which can be comprised of polymers that create rigid gaps between the interface of the coupling medium and the patient's skin.

Since conventional acoustic couplants are inadequate for high resolution ultrasound imaging, the lack of a practical, portable and non-water bath-like couplant has impeded clinical use of high resolution ultrasound imaging techniques, such as for example synthetic aperture or tomographic ultrasound techniques, for many types of diagnostic purposes and procedures, resulting in reliance on X-Ray, CT and MRI which come at high costs or substantial risk to patients. If high-resolution, synthetic aperture or tomographic, ultrasound were to be used, then it requires an impractical and highly-inconvenient set-up to acoustically couple the transducer array to the patient's anatomy to be imaged. For example, when the ultrasound transducer array or the patient's anatomy (to be imaged) is large or possesses particular curvature, e.g., being singly curved or doubly curved, acoustic coupling of the transducer array to the patient anatomy for clinical medical imaging purposes has not been practicable without resorting to a water bath, where both the transducer array and the patient's anatomy are immersed in a volume of water. For example, at present, all synthetic aperture or tomographic ultrasound devices employ a large, non-portable water bath couplant that are limited to only a few applications, such as breast imaging applications. Alternative existing approaches to provide 'quasi-water bath' acoustic couplants fill a polymer skin with water or other fluid, akin to the water filled glove or balloon. FIGS. 1A, 1B and 2 illustrate some of the shortcomings of conventional water-filled sacs as acoustic couplants for use in high-resolution, clinical ultrasound imaging.

FIGS. 1A and 1B show diagrams illustrating a typical quasi-water bath acoustic couplant example that exhibits a lack of conformability to a patient's skin. This example depicts a conventional balloon-like acoustic couplant interface that contains water (e.g., degassed deionized (DI) water) or a semi-fluid (e.g. gel) acoustic coupling medium. As shown FIG. 1A, the balloon-like couplant, in this example, includes a polymer balloon-like outer membrane that encompasses degassed water or other semi-fluid within the polymer outer membrane. The acoustic coupling material entrapped within the outer membrane provides a pressure on the inner surface of the outer membrane, such that the shape of the balloon couplant is defined by the external forces exerted upon the balloon—in this example, the external forces include a normal force ($F_N$) exerted by a flat surface in contact with the balloon couplant and outer force ($F_L$) from the outer environment. The outer membrane of the balloon couplant is typically flexible, and can be bent to attempt to fit around singly or doubly curved surfaces, as shown by the diagram in FIG. 1B. However, such bending always creates creases and hence entrained air at inflexion points along the outer membrane and within the fluidic interior of the balloon couplant due to fundamental topological incompatibility of the two surfaces.

Furthermore, for non-linear arrays and non-planar surfaces, technical issues become too challenging for simple balloon couplants to surmount. Take for instance a semicircular array for Acoustic Coherent Tomography (ACT) which has several array elements that need to couple to a swath of variegated patient interface geometries during a multi-anatomic target examination. The first challenge with balloon couplants is contorting it's at-rest geometry to the transducer interface surface without creasing on the patient interface surface, as shown, for example, in FIG. 1B. Creases will trap air that produce artifacts and shadowing in ultrasound images. For example, even if a few mil-thick (e.g., ≈0.001 inch-thick) polymer membrane was designed to fit in the array without creasing, the balloon couplant still lacks conformability needed to successfully image curved anatomic targets of large variety of shapes since the encapsulated acoustic medium is essentially an incompressible fluid (e.g., $k \approx 50 \times 10^{-6}$ $atm^{-1}$) and conservation of volume principles apply.

For polymers with thick walls, high young modulus, and low strain before failure the load on the transducer side of the balloon couplant is directly transmitted to the patient interface without dispersing the load over a larger surface area and without conforming to the non-symmetric patient geometry. Low elastic modulus, high strain before failure, and thin walled polymers might deform more, but are not conformable enough to bridge large gaps between the rigid, symmetrical transducer interface and the asymmetric, deformable patient interface, and are more prone to bursting and rolling during examinations, as illustrated in FIG. 2.

FIG. 2 shows diagrams illustrating a conventional acoustic couplant, such as a balloon couplant, that is comprised of polymers that create rigid gaps between the interface of the coupling medium and the patient's skin. Diagram 200A shows the example balloon-like acoustic couplant in contact with a surface, illustrating maximum compression on the balloon couplant between applied external forces from a surface in contact with the couplant (normal force $F_N$) and forces ($F_L$) from the surrounding environment. Diagram 200B shows the example balloon acoustic couplant with folds/creases/ridges formed by the outer polymer membrane of the balloon couplant slacking when balloon couplant is bent to conform to the array, trapping air that acts as a strong acoustic reflector. Diagram 200B also shows an example of the balloon acoustic couplant unable to uniformly couple to the target volume because the balloon couplant is unable to conform to the contour of the target to fill in the divot and escarpment. Diagram 200C shows an example balloon couplant in contact with a target volume (e.g., patient's skin of a body part), illustrating how the balloon couplant will have gaps between the couplant and target volume due to divots and/or changes in the contour of the target.

Another example of the fundamental topological incompatibility of a balloon couplant between two surfaces is exacerbated when a doubly or multiply curved (e.g., hemispherical-like) shaped transducer is applied to multiply curved, anatomical structures such as shoulders, knees, elbows, elbows, small parts, etc. In such instances, multiple creases and divots would by necessity occur that will degrade ultrasound images due to couplant induced artifacts.

A more conformable and durable standoff was needed, so thin, semisolid, hydrogel pucks or sheets (e.g., ~1.0–1.5 cm) have been developed to accommodate traditional US imaging in the near field. These hydrogel puck or sheet standoffs aim at minimizing the impedance mismatch between the rigid, symmetrical transducer interface and the asymmetrical, conformable patient interface for linear arrays. More conformable than balloon couplants, thin hydrogel sheets can fill in divots and escarpments along planar surfaces and form to eclectic curved topography. Additionally, depending on the hydrogel chemistry and morphology, hydrogels can either be sticky for long, static US diagnostic scans or generate a lubricating layer via syneresis when conducting short, dynamic scans under pressure.

Yet, despite greater conformability than balloon couplants, hydrogels on the current market have a large bulk modulus which increases hydrogel rigidity as the thickness increases. Coupled with low fracture toughness and paraben preservatives, the stiffness and brittleness, the ease of crack propagation, and the ambiguity of health safety render these conventional hydrogel standoffs useless in applications where a thick (e.g., >2 cm), tough, and conformable semi-rigid standoff is needed for non-linear arrays like the aforementioned ACT semicircular array.

Disclosed are articles, devices and systems providing a semi-rigid acoustic coupling medium (SACM), also referred to as a semi-rigid acoustic couplant (SAC), for ultrasound diagnostic and treatment techniques. In some embodiments, the disclosed SACM articles include a hydrogel interface pad that is semi-solid and sonolucent and can minimize impedance-mismatching of acoustic signals propagating between the acoustic transducer elements and the body having the target volume of interest (VOI).

Implementations of a semi-rigid material with engineered acoustic and mechanical properties can enable tomographic or synthetic aperture ultrasound imaging of general anatomical shapes. For example, human or animal patient anatomy to be imaged by a tomographic or synthetic aperture ultrasound device come in almost an unlimited number of three-dimensional curvilinear shapes and sizes.

In some implementations, the example embodiments of the disclosed SACs can be coupled to an acoustic transducer probe device (e.g., ultrasound scanner). Details of example embodiments of an acoustic transducer probe device that can attach and utilize the example SACM are described in U.S. Publication No. 2016/0242736A1, which is incorporated by reference as part of the technical disclosure of this patent document.

The transducer array aperture surface of an ultrasound scanner used for tomographic and/or synthetic aperture ultrasound imaging can be configured to have a 3D curvilinear shape, which can be a simple 3D curvilinear shape or complex 3D curvilinear shape defined by the number of transducers in the array and their angular arrangement with one another to create a curvilinear transducer array surface. For example, the transducer array aperture can be described by a closed analytically-described curve lying in a plane, such as a cylinder or an ellipse, or by a synthetically-described curve lying in a plane, such as a spline. For example, the transducer array aperture can be composed of one or more segments of analytically- or synthetically-described curves not necessarily lying in a plane, such as for example a conical spiral. Yet, for practical reasons, the number of transducer array apertures are of a limited number.

The disclosed SACs can address the challenges for acoustically coupling a limited number of tomographic or synthetic aperture ultrasound transducer arrays to a relatively unlimited number of anatomical shapes and sizes of the various kind of subjects (e.g., humans, animals, etc.). The disclosed SACs are engineered to have mechanical properties that allow it to sufficiently deform to entirely conform to both the array aperture and the surface of patient without gaps or air entrainment, while having a minimal acoustic attenuation and optimal acoustic impedance matching. Moreover, the disclosed SACs, when attached to the transducer array, allow the array to be conveniently positioned multiple times during the imaging procedure over varying tissue geometry to capture the desired anatomical region of interest.

In some embodiments, the disclosed SACs include an engineered polymer network having the ability to form elaborate geometries and entrap water to a high percentage (e.g., 85% or greater) that provides acoustic impedance matching between ultrasound transducer elements and the target biological volume. The disclosed SACs are semi-flexible, -stretchable and -bendable, for example, while also being semi-stiff, e.g., analogous to a bendable rubber. In some embodiments, the semi-flexible SAC is stiffer than a soft elastomer, but soft enough to stretch and bend considerably without breaking. The disclosed SACs provide additional advantages in their manner of manufacture, distribution and application based on their low-cost of fabrication, simultaneous step of sterilization and curing, stable storage, and biocompatibility.

Example Embodiments of Semi Rigid Acoustic Couplant

Figure 3A:
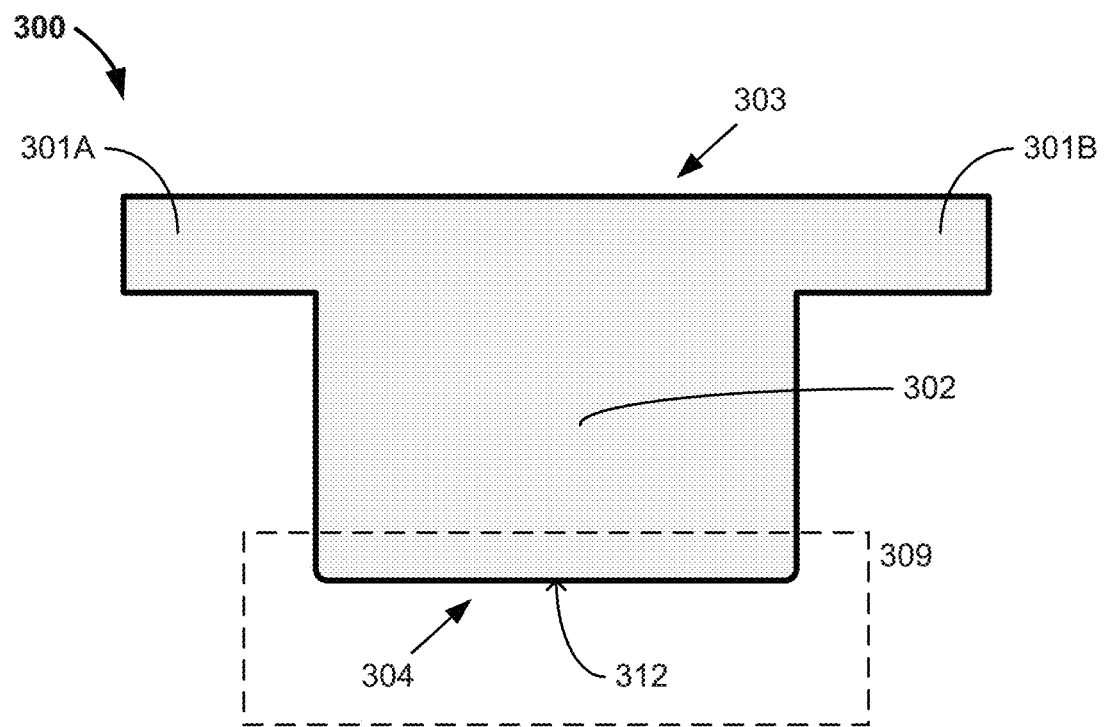
FIG. 3A-3D show diagrams depicting an example embodiment of a semi-rigid acoustic coupling medium in accordance with the present technology.

FIG. 3A shows a diagram depicting an example embodiment of a semi-rigid acoustic couplant article 300 in accordance with the present technology. The SAC article 300 is configured from a single, uniform acoustic coupling material having an interface portion 302 and attachment portions 301A and 301B formed on both sides of the interface portion 302. In some embodiments, like that shown in FIG. 3A (albeit not drawn to scale), the SAC article 300 is structured to have a "T-like" shape where the attachment portions 301A and 301B are located at one end 303 of the interface portion 302, which can provide a wider acoustic coupling medium in the elevation dimension for tomographic and/or synthetic aperture ultrasound imaging applications. The SAC article 300 is configured to physically contact and conform to an array of transducer elements at the surface along the end 303 of the SAC article 300 to acoustically interface an ultrasound probe device to the acoustic couplant. The SAC article 300 is configured to physically contact and conform to a receiving body at another end 304 of the SAC article 300 to acoustically interface the acoustic couplant for propagating acoustic signals between the array of transducer elements and the receiving body. In various embodiments, the transducer-interfacing surface at end 303 is positioned at an opposing side to the receiving body-interfacing surface at end 304 across the interface portion 302 of the SAC article 300.

When the SAC article 300 is coupled to an acoustic probe device, the end 304 is an outward-facing surface (outward surface 312) providing the receiving body-interfacing surface of the SAC article 300. In some embodiments, the outward surface 312 of the interface portion 302 includes a singly-curved face or multiply-curved face in one or more directions between the ends defined by the attachment portions 301A and 301B, like that shown in the example of FIG. 3B. In some embodiments, a multiply-curved face of the outward surface 312 includes a convex face in the two planar directions that define the surface.

Figure 3B:
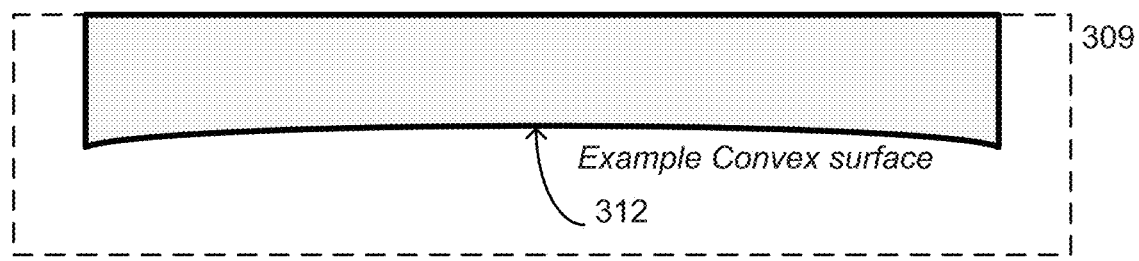

FIG. 3B shows a diagram of the inset 309 shown in FIG. 3A, depicting a cross-sectional (planar) view of a multiply-curved face that forms a convex region of the outward surface 312. The convex shape of this example is one of an infinite number of mathematically possible, singly- or multiply-curved shapes, e.g., such as concave or convex shapes, that can be presented on the outward surface 312 of the SAC article 300.

Figure 3C:
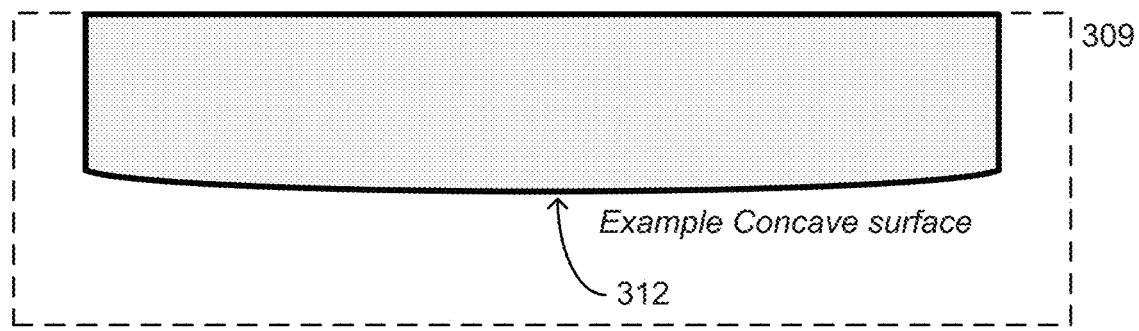

FIG. 3C shows a diagram of the inset 309 shown in FIG. 3A, depicting a cross-sectional (planar) view of a multiply-curved face that forms a concave region of the outward surface 312. The concave shape of this example is an example where the curvature of the outward surface 312 is in multiple directions (although only a planar view is shown in the diagram).

The singly-curved surface or multiply-curved surface (e.g., doubly-curved surface) can additionally or alternatively be configured on the first end to improve conformation of the semi-rigid acoustic couplant to the transducer array, e.g., particularly for transducer elements having curved or otherwise non-flat shapes.

Figure 7:
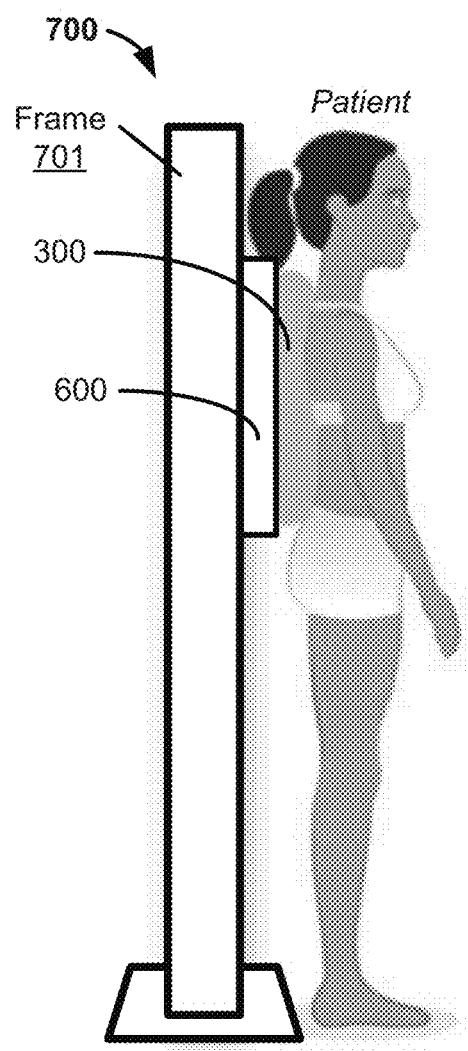
FIG. 7 shows a diagram illustrating an acoustic imaging system employing an example embodiment of the semi-rigid acoustic coupling medium in accordance with the present technology for generating synthetic aperture or tomographic, high-resolution, images of various human anatomical structures.

These examples of the SAC article 300 overcomes the aforementioned problems of interfacing rigid, singly- or doubly-curved shaped transducer arrays to complex anatomical structures such as shoulders, knees, elbows, elbows, small parts, etc. In such instances, the deformable nature of semi-rigid acoustic couplants permits them to conform to a singly-, doubly- or multiply-curved transducer array and to arbitrarily shaped anatomical structures. By using semi-rigid acoustic couplants, synthetic aperture or tomographic imaging techniques can be employed without requiring both the transducer array and anatomical structure to be immersed in a water bath, as currently done in existing tomographic imaging devices. Arbitrarily shaped, relatively large arrays (e.g., >100 mm in extent, which are notably larger than almost all current US arrays) using an example SACM couplant, such as the SAC article 300, can be used to generate synthetic aperture or tomographic, high-resolution, images of various human anatomical structures without requiring a water bath couplant, for example, as illustrated in FIG. 7 and discussed later below. Therefore, such semi-rigid acoustic couplants enable many new portable, high definition, diagnostic and point-of-care (e.g., inter-operative) clinical imaging applications that previously were not possible.

In various embodiments, the SAC article 300 includes one or more hydrogel materials in a single SACM couplant. For example, in some embodiments, a single hydrogel material can be fabricated in the desired shape (e.g., including but not limited to the example T-shape shown in FIG. 3A), where the single hydrogel material that forms the SAC article 300 is structured to have one or more attachment portions located at the end 303 and the interface portion 302 spanning away from the end 303 and terminating at the end 304, which provides the outward surface 312 to interface with the receiving body. In various example embodiments, the outward surface 312 of the interface portion 302 is structured to (i) be flat, at least at a portion of the outward surface, (ii) have a single curve along one direction of the outward surface, at least at a portion of the outward surface, and/or (iii) have multiple curves in multiple directions along the outward surface, at least at a portion of the outward surface. The SAC article 300 is able to conform to the receiving body for propagation of the acoustic signals into and from the receiving body, and such that the one or more attachment portions are configured to be secured by an acoustic probe device having the array of transducer elements to transmit and receive the propagated acoustic signals, e.g., where the SAC article 300 conforms to both the receiving body and array of transducer elements of an acoustic probe device, including by deformations like stretching and bending of the SAC article 300, without resulting in gaps, creases, or air entrainments at any interface of the SACM with the receiving body and the transducer elements.

Yet, in some embodiments, for example, the SAC article 300 includes a plurality of individual hydrogel materials, where the individual hydrogel materials of the plurality couple and conform to each other without resulting in gaps, creases, or air entrainments in between to form a single hydrogel material. In this manner, the SAC article 300 including the plurality of individual hydrogel materials is able to perform like the single hydrogel material embodiment, e.g., where the SAC article 300 conforms to both the receiving body and array of transducer elements of an acoustic probe device, including by deformations like stretching and bending of the SAC article 300, without resulting in gaps, creases, or air entrainments at any interface of the SACM with the receiving body and the transducer elements. Example compositions of the individual hydrogel materials are described later below.

Figure 3D:
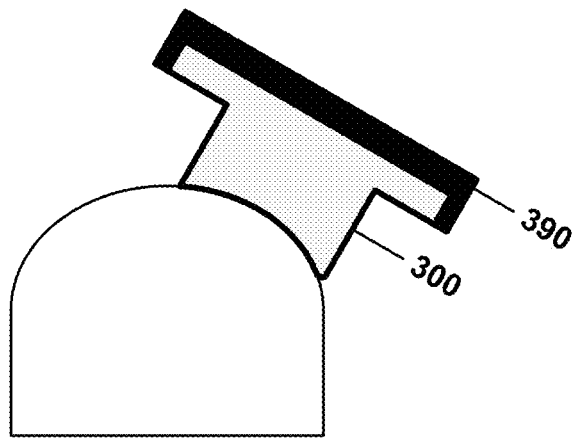
Figure 3D:
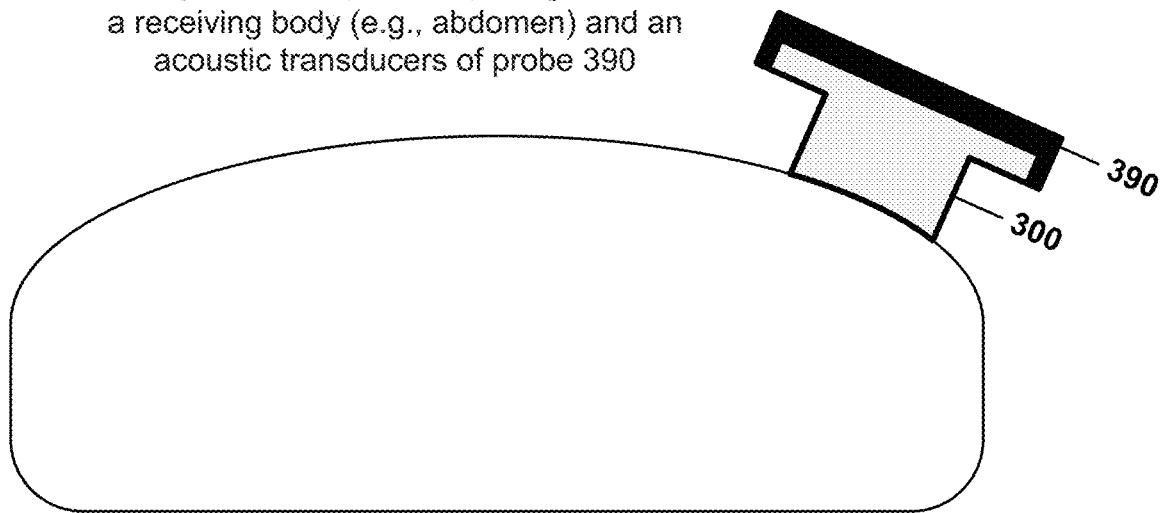

FIG. 3D shows a diagram of two example implementations where the SAC 300 is interfaced with an array of acoustic transducers in an acoustic probe device 390, e.g., like the example acoustic probe device 600 shown later in FIGS. 6A-6C or the acoustic probe devices shown in the disclosure of U.S. Patent Publication No. 2016/0242736A1, the contents of which are incorporated by reference as part of this disclosure for all purposes. The SAC 300 is interfaced with the array of acoustic transducers in the acoustic probe device 390 in a manner such that the acoustic coupling medium material, i.e., the SAC 300, conforms between a receiving body (e.g., breast and an abdomen) and the acoustic transducers of the probe 390.

In some embodiments, the SAC article 300, when interfaced to an acoustic probe device, is operable to propagate acoustic signals with an acoustic impedance matching of 10 MRayls or less (e.g., more preferably 4 MRayls or less for certain applications, and capable of 2 MRayls or less or 1.6 MRayls or less). In such examples, the SAC article 300, when interfaced to the acoustic probe device, is operable to propagate acoustic signals with an acoustic attenuation in a range of about 0.0001-1.00 dB/cm/MHz. In such devices, the SAC conforms to the surfaces of both an acoustic probe device having one or more transducer elements and receiving body (having the target biological volume) based on its semi-rigidity. In some embodiments, the SAC article 300 can be configured to include one or more of the following properties: stretchability of 10% to 1000% elongation or greater, e.g., 2500%; compression of 20% to 99.99%, and a Young's modulus of 30 kPa to 500 kPa, or in some embodiments lower than 30 kPa, e.g., as low as 1 kPa.

In some embodiments in accordance with the present technology, the SAC 300 is configured as a hydrogel formed of a composition that includes a monomer, a block copolymer, and a dispersive phase. In some embodiments, the hydrogel composition includes the monomer, the block copolymer, the dispersive phase and a covalent crosslinker agent, a cationic crosslinking agent, a catalyst, and/or a free radical initiator.

For example, the monomer can serve as the primary, structural network for the hydrogel. In some embodiments, the monomer is an acrylamide. Non-limiting examples of acrylamide monomers include dimethylacrylamide (DMA), diethylacrylamide (DEAA), phenyl acrylamide, tert-butyl acrylamide, octadecylacrylamide, isopropylacrylamide, or diphenylmethylacrylamide. The monomer is sometimes referred to as the "1° network". In some embodiments, for example, the 1° network monomer includes DMA.

For example, the block copolymer can provide a secondary, grated sacrificial network for the hydrogel. In some embodiments, the block copolymer is an alginate. Non-limiting examples of alginates include sodium alginate (SA), potassium alginate, calcium alginate, ammonium alginate, low acetylated gellan gum, high acetylated gellan gum, modified starches, agar, k-Carrageenan, I-Carrageenan, low methoxy pectin, high methoxy pectin, methyl cellulose, hydroxypropyl methyl cellulose, cellulose/gelatin, or propylene glycol alginate. The block copolymer is sometimes referred to as the "2° network". In some embodiments, for example, the block copolymer includes SA.

In some embodiments, the dispersive phase is water (e.g., deionized water (DI $H_2O$)), which can be present in an amount of about 75.65 wt % to about 95.98 wt % of the total weight of the hydrogel interface pad.

In some embodiments, the covalent crosslinker agent is an acrylamide. Non-limiting examples of acrylamide covalent crosslinkers include N',N'-methylene bisacrylamide (MBA), bisacrylamide, ethylene bisacrylamide, piperazine diacrylamide, or ethylene glycol bisacrylamide. The covalent crosslinker agent is sometimes referred to as the 1°-network crosslinker. In some embodiments, for example, the 1°-network crosslinker agent includes SA.

In some embodiments, the cationic crosslinking agent is a monovalent, divalent, trivalent metal. For example, a cationic crosslinking agent can be a transition metal, an alkali metal, or an alkaline earth metal where the metal is the $1^+$, $2^+$, or $3^+$ oxidation state. In some embodiments, the cationic crosslinking agent is lithium, sodium, potassium, magnesium, calcium, zinc, zirconium, iron, cobalt, nickel, titanium, or copper. In some embodiments, the cationic crosslinking agent is in the form of any monovalent divalent, or trivalent salt. For example, in some embodiments the cationic crosslinking agent is any sulfate, phosphate, chloride, bromide, triflate, amine, or carboxylate salt. In some embodiments, the cationic crosslinking agent is calcium sulfate (CA), calcium phosphate, calcium chloride, calcium bromide, or calcium triflate. The cationic crosslinking agent is sometimes referred to as the 2°-network activator. In some embodiments, for example, the 2°-network activator includes CA.

For example, the catalyst can promote and/or increase the rate of the chemical reaction that forms the hydrogel composition. In some embodiments, the catalyst is an amine. Non-limiting examples of amine catalyst include aliphatic amines, N',N',N,N-tetramethylethylenediamine (TMED), benzyldimethylamine, methylamine, or triethyl amine.

For example, the free radical initiator can generate free radicals that initiate the formation of the polymeric network of the hydrogel composition. Non-limiting examples of free radical initiators includes ammonium persulfate (APS), peroxides such as dialkyl peroxides, hydroperoxides, diacyl periods, or azo-compounds (i.e., —N=N— moieties). In some embodiments, the initiator is a photoinitiator. Non-limiting examples of photo initiators include ribofalvin-5'-phosphate, ribofalvin-5'-phosphate sodium, ethyl (2,4,5-trimethylbenzoyl) phenyl phosphinate (TPO-L), bis-acylphosphine oxide (BAPO), 2-hydroxy-2-methyl propiophenone, methylbenzoyl formate, isoamyl 4-(dimethylamino) benzoate, 2-ethyl hexyl-4-(dimethylamino) benzoate, or diphenyl(2,4,6-trimethylbenzoyl) phosphine oxide (TPO). Additional, non-limiting examples of suitable photoinitiators include 1-hydroxycyclohexyl phenyl ketone (Irgacure 184), 2,2-dimethoxy-2-phenylacetophenone (Irgacure 651), and 2-methyl-1-[4-(methylthio)phenyl]-2-(4-morpholinyl)-1-propanone (Irgacure 907), hydroxyacetophenone, phosphineoxide, benzophenone, and lithium phenyl-2,4,6-trimethylbenzoylphosphinate (LAP). The free radical initiator is sometimes referred to as the 1°-network activator. In some embodiments, for example, the 1°-network activator includes TMED In some exemplary embodiments of the present disclosure, a semi-rigid hydrogel interface pad is made up of two water soluble polymer networks: a primary (1° network) scaffold and a secondary (2° network) sacrificial graft. In some embodiments, the hydrogel interface pad includes a dimethyl acrylamide monomer (DMAm), a sodium alginate block copolymer (P(SA)), and water. For example, the DMA concentration can be engineered to affect the elasticity and conformability. In some embodiments, the hydrogel interface pad further comprises MBA, TMED, CA, and APS.

Figure 4:
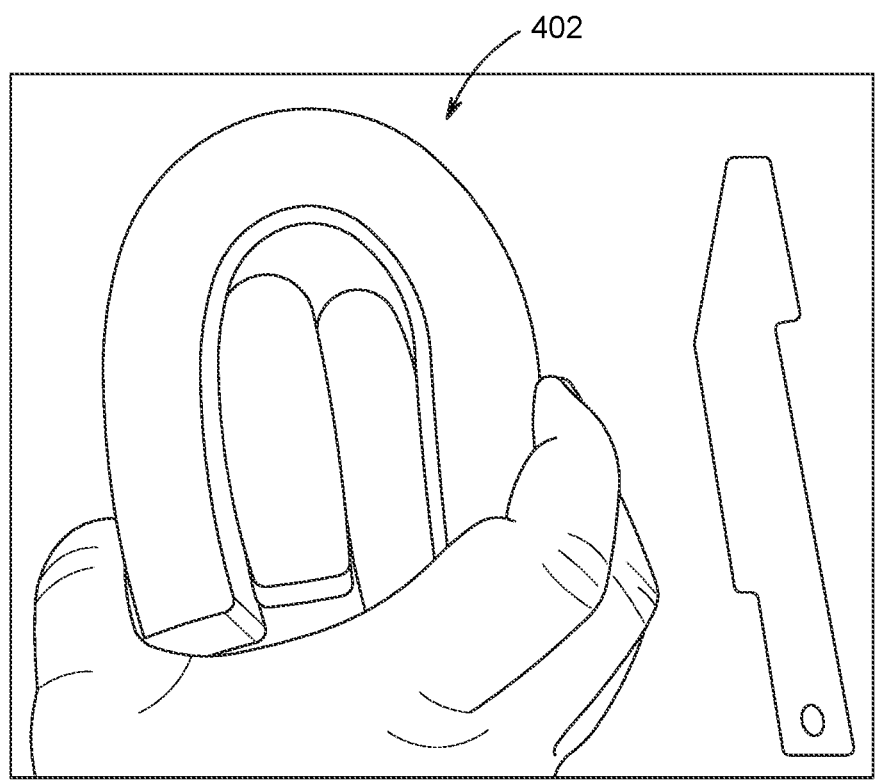
FIG. 4 shows an image of an example ionically, cross-linked semi-rigid acoustic coupling medium.

FIG. 4 shows an image of an example embodiment of a SAC in accordance with the present technology produced as an ionically, crosslinked hydrogel interface pad (HIP) 402.

In example implementations, mechanical and acoustic properties of the HIP 402 and a second example hydrogel interface pad 401 used as a control (not shown) were compared, as shown in Table 1. The example HIP 401 is composed of Poly(Acrylamide) (Poly(AA)) with low viscosity P(SA) 2° network with good elastic, conformability, and clarity properties. Rippling on exposed surface of the example HIP 401 was due to surface tension differentials during the gelation process. The example HIP 402 was configured to have the same composition of P(SA) as the HIP 401 but includes Poly(DMAm) instead of Poly(AA).

Table 1 shows tested acoustic and mechanical properties of the example HIP sample 402 and for the example control hydrogel sample 401. Note, in Table 1, "SOS" stands for speed of sound; "Z" is acoustic impedance, "ATTN" is attenuation, "E" is the Young's Modulus, and "ε" is the engineering strain.

TABLE 1

| Hydrogel Sample (#) | SOS (m/s) | Z (MRayls) | ATTN (dB/cm/MHz) | E (kPa) | ε (mm) |
|---|---|---|---|---|---|
| 401 | 1548 | 1.595 | 0.14 | 48 | −15 |
| 402 | 1549 | 1.597 | 0.14 | 32 | −15 |

Figure 5A:
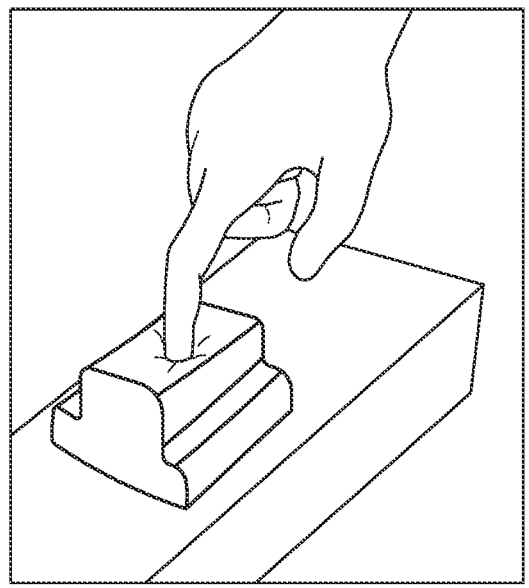
FIGS. 5A-5F show images of an example semi-rigid acoustic coupling medium under mechanical stress.
Figure 5B:
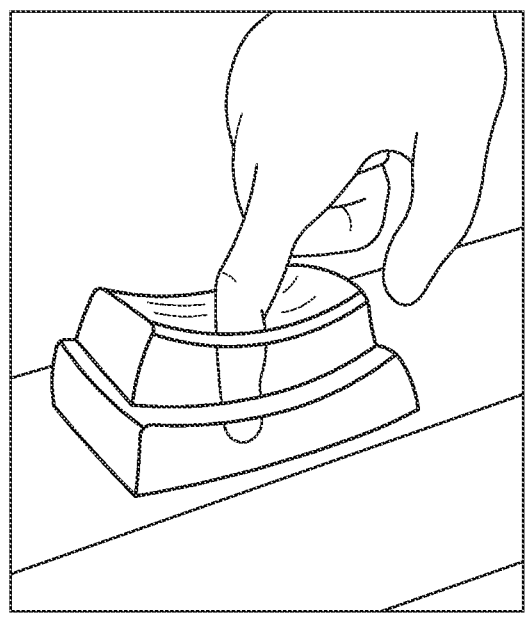
Figure 5C:
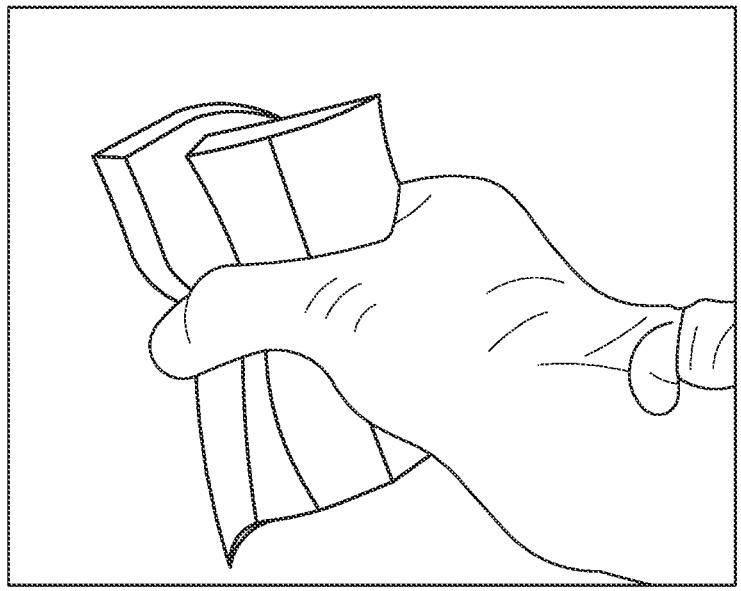
Figure 5D:
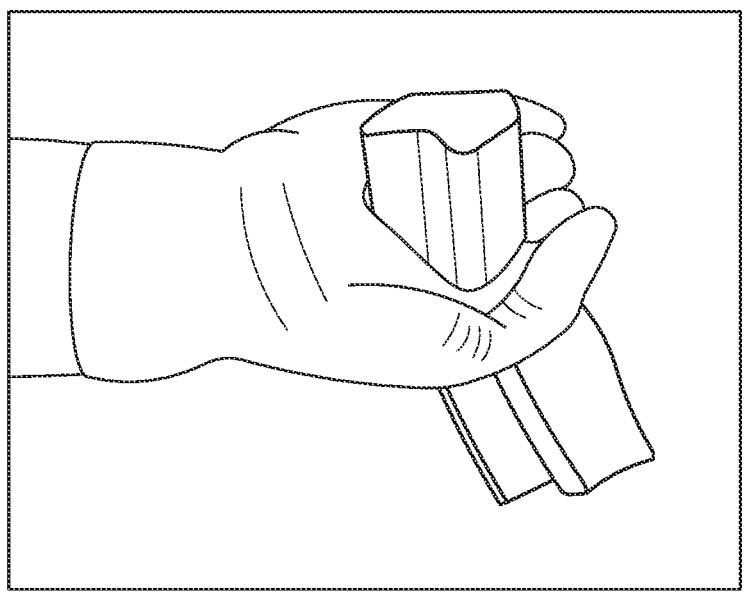
Figure 5E:
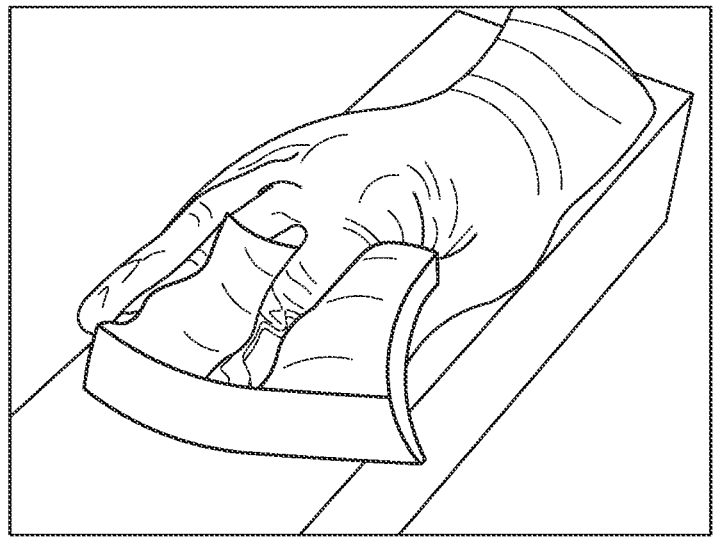
Figure 5F:
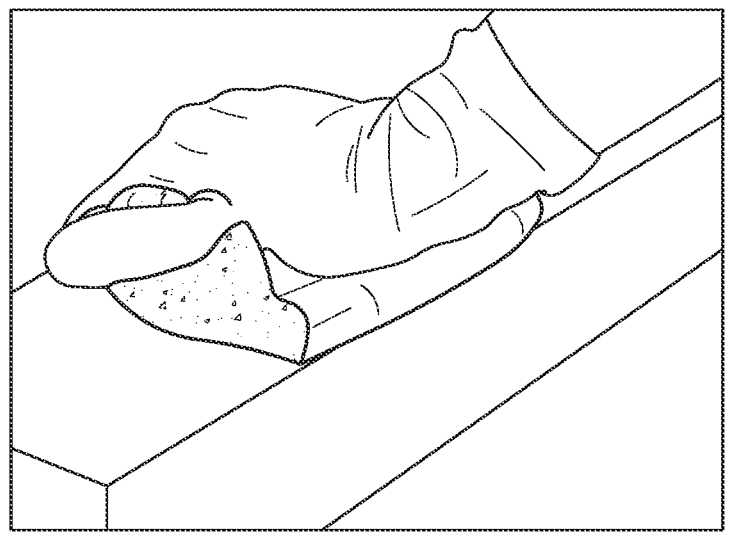

FIGS. 5A-5F show images of the pliability, stretchability, deformability, and robustness of an example semi-rigid acoustic coupling medium article. Specifically, FIG. 5A shows the example SACM prior to localized compression, contrasting FIG. 5B which shows the SACM during localized compression. Similarly, FIG. 5C shows the SACM prior to squeezing, contrasting FIG. 5D which shows the SACM during squeezing. Lastly, FIG. 5E shows the SACM conformability characteristics and FIG. 5F shows the SACM under full compression. Taken together, these experiments support that the SACM is resistant to fracturing, which can be attributed to an overall increase in toughness and elasticity. Notably, the example SACM is able to undergo all of these physical deformations while maintaining its full acoustic propagation properties, thereby allowing an acoustic imaging system employing the SACM to form an acoustic image without artifacts.

Figure 6A:
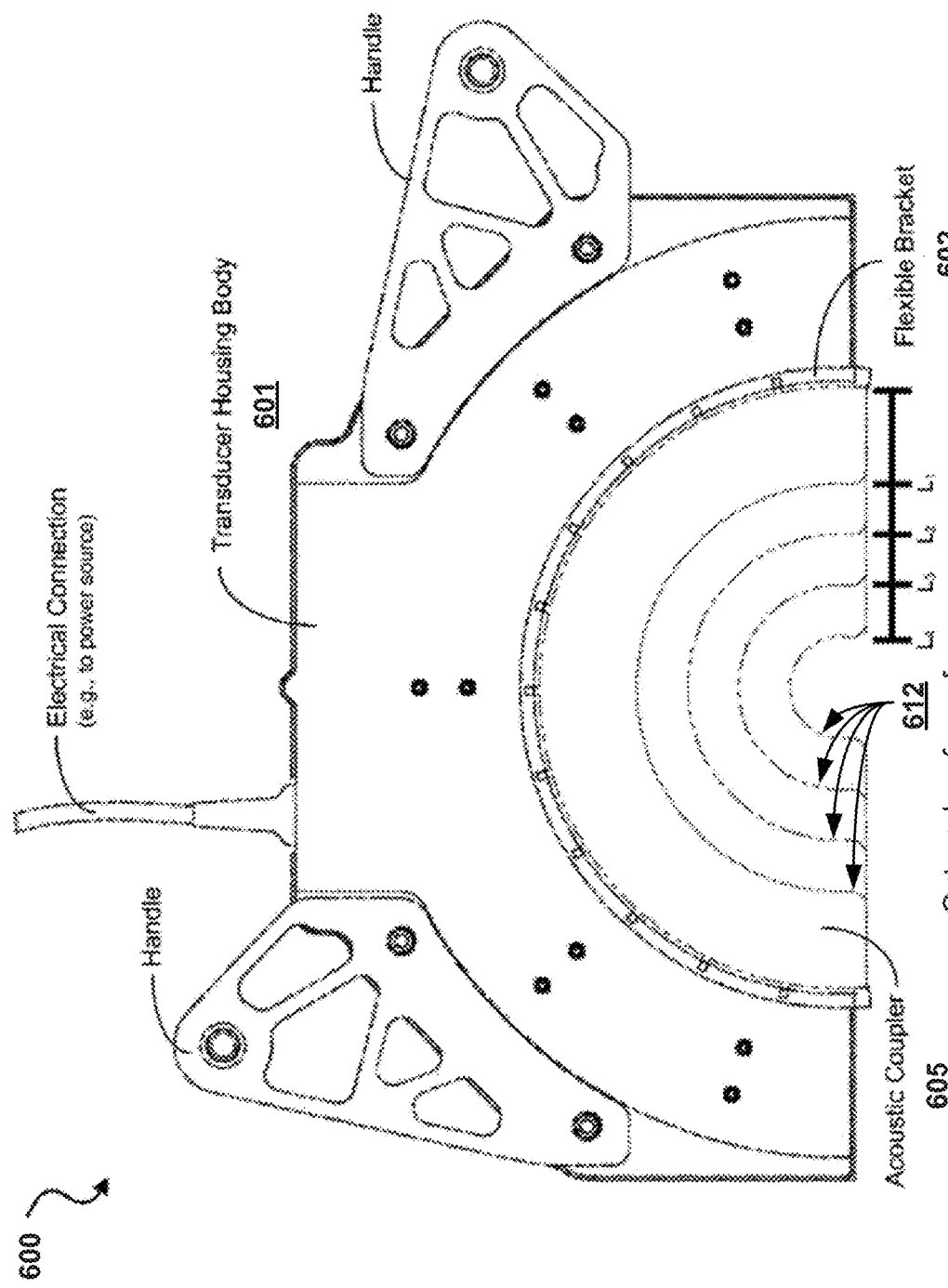
FIGS. 6A-6C show schematic diagrams of an acoustic probe device including in accordance with the example embodiments of the disclosed acoustic couplant medium technology.
Figure 6B:
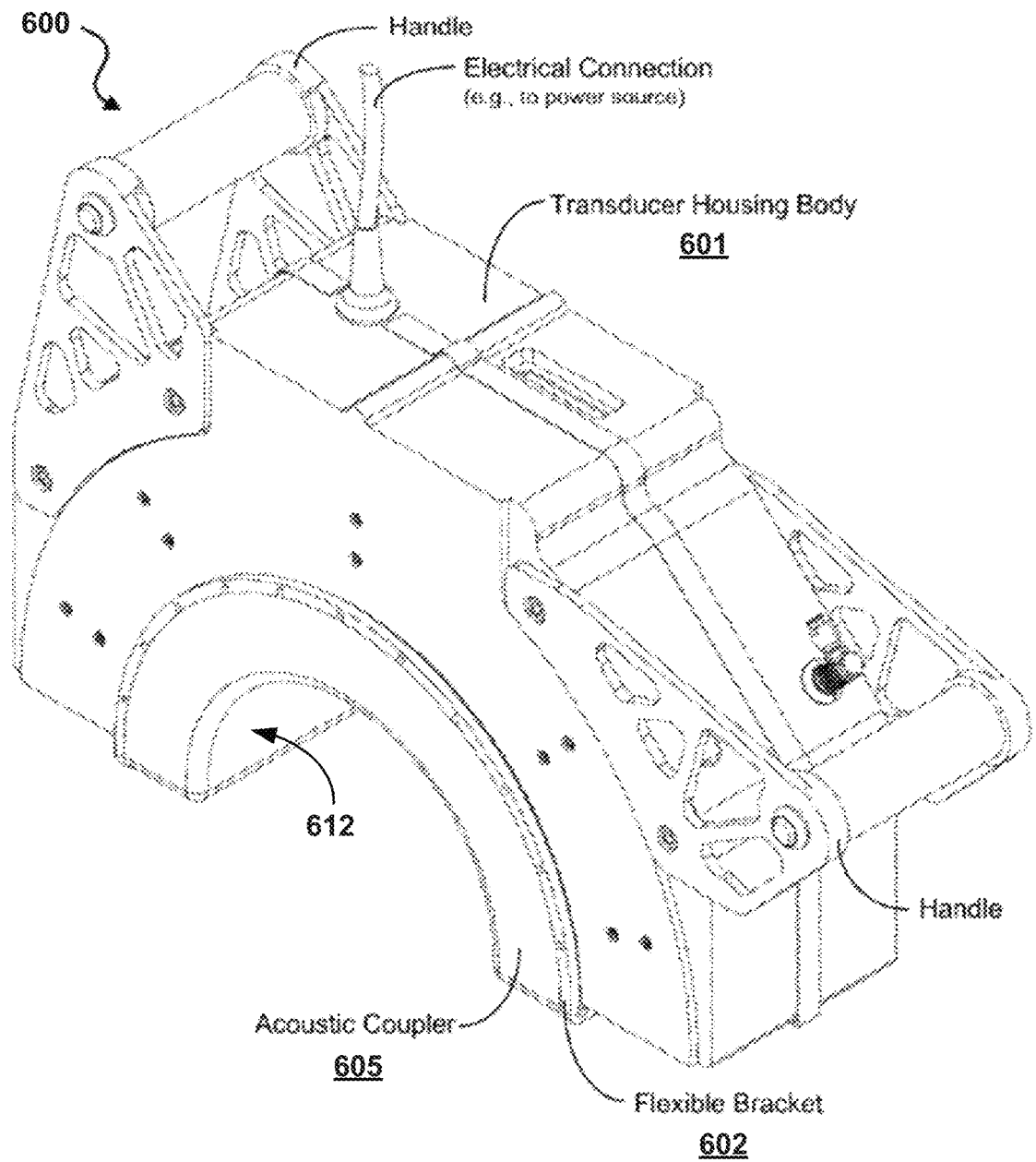
Figure 6C:
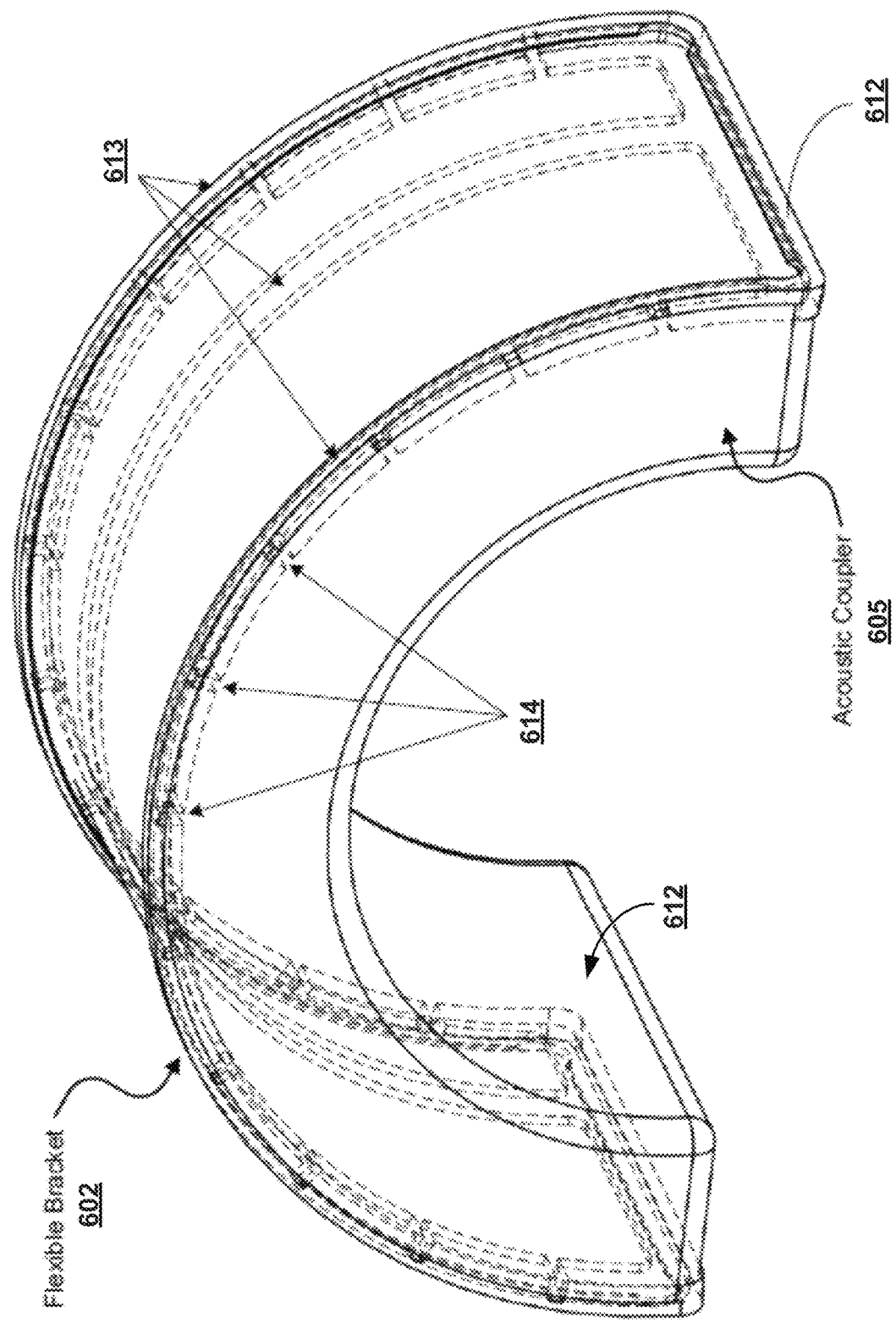

FIGS. 6A-6C show schematic diagrams of an acoustic probe device 600 in accordance with the example embodiments of the disclosed semi-rigid acoustic coupling medium (SACM) for ultrasound diagnostic and treatment techniques. The probe device 600 includes a housing structure 601 to contain and position one or more transducers for transmitting and receiving acoustic signals to/from a mass (e.g., body part) to which the acoustic probe device 600 is applied. The couplant device 600 includes an acoustic coupling article 605 that is an embodiment of any of the disclosed SACMs, e.g., including but not limited to the semi-rigid acoustic couplant article 300 shown in FIGS. 3A-3D. The acoustic coupling medium article 605 is attached to the housing structure 601 such that the acoustic coupling article 605 is in contact with the external surface area of the transducer elements disposed in the housing structure 601.

In this non-limiting example, the housing structure 601 includes a curved section where transducer elements (not shown) of an acoustic transmit and/or receive transducer array are positioned. The curved section of the housing structure 601 can be configured to various sizes and/or curvatures tailored to a particular body region or part where the couplant device 600 is to be applied in acoustic imaging, measurement, and/or therapy implementations. For example, the length, depth, and arc of the curved section of the housing structure 601 can be configured to make complete contact with a region of interest on an anatomical structure, e.g., such as a breast, arm, leg, neck, throat, knee joint, hip joint, ankle, waist, shoulder, or other anatomical structure of a human or animal (e.g., canine) subject to image or apply ultrasonic treatment to target volumes within such structures, such as splenic masses, cancerous or non-cancerous tumors, legions, sprains, tears, bone outlines and other signs of damage or maladies. For example, the curved section of the housing structure 601 can include an aperture length in a range of a few centimeters to tens or hundreds of centimeters (e.g., such as an 18 cm baseline as depicted in FIG. 6A), an aperture depth in a range of a few centimeters to tens or hundreds of centimeters, and an arc or curvature of 1/(half or a few centimeters) to 1/(tens or hundreds of centimeters), e.g., $1/0.5$ $cm^{-1}$ to $1/18$ $cm^{-1}$. Notably, in some examples, the transducer section of the probe device 600 can be flat, angled or arranged in other geometries in addition or alternative from being curved.

Similarly, in another non-limiting example, the housing structure 601 can include a relatively flat section where transducer elements (not shown) of an acoustic transmit and/or receive transducer array are positioned, such that the transducer-interfacing surface of the acoustic coupling article 605 is matched in geometry to conform with the transducer elements.

In any geometrical embodiment of the acoustic coupling article 605, the semi-rigid acoustic coupling article 605 may include a convex face on the outward surface 612 of the article 605 that interfaces with the receiving medium.

The acoustic coupling article 605 is operable to conduct acoustic signals between the transducer elements of the probe device 600 and a receiving medium (e.g., body region or part of the subject, e.g., such as the subject's midsection, head, or appendage) where the probe device 600 is to be placed in contact to transmit and receive the acoustic signals propagating toward and from a target volume of interest in the subject. The acoustic coupling article 605 is able to conform to the receiving medium to provide acoustic impedance matching between the transducer elements and the receiving medium (e.g., the skin of the subject, including body hair protruded from the skin).

In some embodiments of the probe device 600, for example, the housing structure 601 includes a flexible bracket 602 that attaches to a portion of the housing structure 601 body on the transducer facing side, e.g., the curved section of the housing structure 601 body in the illustrative example in FIGS. 6A-6C. In some implementations, for example, the acoustic coupling article 605 can be molded into the flexible bracket 602, which can also include the acoustic coupling article 605 being adhesively attached (e.g., glued) to the flexible bracket 602 at portions of the acoustic coupling article 605 away from acoustic signal propagation with the transducer elements. The flexible bracket 602 is structured to flex such that it can conform to the receiving body that it surrounds. For example, the flexible bracket 602 can include flexible materials, e.g., including, but not limited to, ABS plastic, polyurethane, nylon, and/or acetyl copolymer.

As illustrated in FIG. 6C, in some embodiments, the acoustic coupling article 605 is coupled to the flexible bracket 602 via notch attachments and/or arches. For example, the flexible bracket 602 can include a base component 612 to attach to the ends of the acoustic coupler 605. In some embodiments, the base component 612 can include clips to secure and/or adhere the acoustic coupler 605. In the example shown in FIG. 6C, the flexible bracket 602 includes one or more arch components 613 configured to a size and curvature to span across the curved section of the housing structure 601 body. The one or more arch components 613 are positioned at one or more respective locations on the base component 612 away from where the transducer elements are to be positioned when the flexible bracket 602 is attached to the housing structure 601. In some embodiments, the flexible bracket 602 can include a pattern of notches 614, e.g., disposed on one side of the arch component(s) 613, to allow the flexible bracket 602 to bend easily without breaking. The spacing of the notches 614 can be configured based on the curvature section of the housing structure 601. In some embodiments, for example, the flexible bracket 602 can include an undercut lip with a chamfer, e.g., located on the other side of the arch component(s) 113, so that when it is flexed into the shape of the array and pressed into position, the chamfered lip flexes over the lip on the curved section of the housing structure 601 and secures the flexible bracket 602, and thereby the acoustic coupler 605, in place.

In some implementations, for example, the acoustic coupling article 605 can be bonded or molded into the flexible bracket 602 when cross-linking of SACM occurs. In some implementations, for example, the SACM of the acoustic coupling article 605 can also be molded on the subject-facing side to smooth or curve the edges, e.g., which can allow the probe device 600 to contact and release from the subject easier.

In some embodiments, the acoustic coupling article 605 couples to the transducers of the probe device 600 via a flexible, overmolded bracket. For example, the bracket is imbedded in gel-sol during pour-casting; and once the gel-sol cures, the overmolded bracket 602 can then retain the acoustic coupling article 605 to the probe device 600 via snap fit features on the probe device housing.

FIG. 7 shows a diagram illustrating an acoustic imaging system employing an example embodiment of the SAC article 300 for generating synthetic aperture or tomographic, high-resolution, images of various human anatomical structures. In this example, the acoustic imaging system 700 includes a frame 701 to hold the acoustic probe device 600 (having the array of transducers) that is coupled to the example SAC article 300, which conform to the array of transducers and to the patient's body. The frame 701 can be configured in various ways to present the probe device 600 and SAC article 300 to the desired part of the patient's body. The acoustic probe device 600 can be configured such that the array of transducer elements are presented in a flat or curved arrangement, and is not limited by the specific example shown in the diagrams of FIGS. 6A-6C. Here, the SAC article 300 can conform to both a large array, which curves around the patients back as illustrated in the diagram. This example figure depicts how the SAC article 300 would enable synthetic aperture tomographic imaging of selected hard, soft or combined hard and soft tissue anatomical features with our resorting to a water bath. Due to the mechanical and acoustic properties of the SAC article 300, the acoustic imaging system 700 is able to generate such high-resolution images on any part of the patient's anatomy in contact with the SAC article 300 without requiring a water bath or water bath-like inferior couplant.

EXAMPLES

The following examples are illustrative of several embodiments of the present technology. Other exemplary embodiments of the present technology may be presented prior to the following listed examples, or after the following listed examples.

In some embodiments in accordance with the present technology (example A1), an acoustic coupling article includes a semi-rigid acoustic coupling medium (SACM) operable to conform to a receiving body to propagate an acoustic signal within the SACM to and from the receiving body.

Example A2 includes the article of any of examples A1-A10, wherein the SACM is configured in a shape having two attachment portions located at one end of an acoustic interface portion, such that the acoustic interface portion is operable to contact the receiving body to propagate the acoustic signal and the attachment portions are configured to be secured by an acoustic probe device to transmit and receive the propagated acoustic signal.

Example A3 includes the article of any of examples A1-A10, wherein the SACM is operable to propagate the acoustic signal between the receiving body and the SACM with an acoustic impedance matching of 2 MRayls or less.

Example A4 includes the article of any of examples A1-A10, wherein the SACM is operable to conform to both the receiving body and an acoustic probe device having one or more transducer elements without gaps in between the external layer of the SACM and the receiving body and one or more transducers.

Example A5 includes the article of example A5, wherein the SACM is stretchable in a range of 10% to 1000% elongation.

Example A6 includes the article of example A5, wherein the SACM is compressible in a range of 20% to 99.9%.

Example A7 includes the article of any of examples A1-A10, wherein the SACM includes an elasticity with a Young's modulus in a range of 30 kPa to 500 kPa.

Example A8 includes the article of any of examples A1-A10, wherein the SACM includes a biocompatible material.

Example A9 includes the article of any of examples A1-A10, wherein the SACM is sterile within a packaging container.

Example A10 includes the article of any of examples A1-A9, wherein the SACM is clean and non-sterile within a packaging container.

In some embodiments in accordance with the present technology (example B1), an acoustic coupling article includes a semi-rigid acoustic coupling medium (SACM) operable to contact and conform to an array of transducer elements at a first end of the SACM and to a receiving body at a second end of the SACM to propagate acoustic signals within the SACM between the array of transducer elements and the receiving body. The SACM includes one or more hydrogel materials in a single acoustic coupling article, where the SACM is structured to have one or more attachment portions located at the first end and an acoustic interface portion spanning away from the one or more attachment portions and terminating at the second end, such that an outward surface of the acoustic interface portion at the second end is structured to (i) be substantially flat, at least at a portion of the outward surface, (ii) have a single curve along one direction of the outward surface, at least at a portion of the outward surface, and/or (iii) have multiple curves in multiple directions along the outward surface, at least at a portion of the outward surface. The outward surface is operable to conform to the receiving body for propagation of the acoustic signals into and from the receiving body. The one or more attachment portions are configured to be secured by an acoustic probe device having the array of transducer elements to transmit and receive the propagated acoustic signals.

Example B2 includes the article of example B1, which can be embodied as the article in any of examples C1-C15.

In some embodiments in accordance with the present technology (example C1), an acoustic coupling article includes a semi-rigid acoustic coupling medium (SACM) operable to contact and conform to an array of transducer elements at a first end of the SACM and to a receiving body at a second end of the SACM to propagate acoustic signals within the SACM between the array of transducer elements and the receiving body. The SACM includes a single hydrogel material and is structured to have a shape including one or more attachment portions located at the first end and an acoustic interface portion spanning away from the one or more attachment portions and terminating at the second end, such that an outward surface of the acoustic interface portion at the second end is structured to (i) have a single curve along one direction of the outward surface, at least at a portion of the outward surface, and/or (ii) have multiple curves in multiple directions along the outward surface, at least at a portion of the outward surface. The outward surface is operable to conform to the receiving body to propagate the acoustic signals into and from the receiving body. The attachment portions are configured to be secured by an acoustic probe device having the array of transducer elements to transmit and receive the propagated acoustic signals through the single hydrogel material.

Example C2 includes the article of any of examples C1-C15, wherein the SACM is capable to conform to both the receiving body and an acoustic probe device having one or more transducer elements without resulting in gaps, creases, or air entrainments in between an external surface of the SACM and the receiving body and one or more transducers.

Example C3 includes the article of any of examples C1-C15, wherein the multiple curves in multiple directions forms a convex surface on at least a portion of the outward surface of the SACM.

Example C4 includes the article of any of examples C1-C15, wherein the multiple curves in multiple directions forms a concave surface on at least a portion of the outward surface of the SACM.

Example C5 includes the article of any of examples C1-C15, wherein the multiple curves in multiple directions forms a convex surface on at least a first portion of the outward surface and a concave surface on at least a second portion of the outward surface of the SACM.

Example C6 includes the article of any of examples C1-C15, wherein the SACM is structured to have a T-shape including two attachment portions located at the first end, and the acoustic interface portion spans away from the two attachment portions and terminates at the second end.

Example C7 includes the article of any of examples C1-C15, wherein the SACM is operable to propagate the acoustic signals between the receiving body and the SACM with an acoustic impedance matching of 2 MRayls or less.

Example C8 includes the article of any of examples C1-C15, wherein the SACM is operable to propagate the acoustic signals between the receiving body and the SACM with an acoustic attenuation of about 0.001-1.00 dB/cm/MHz.

Example C9 includes the article of any of examples C1-C15, wherein the SACM is stretchable in a range of 10% to 1000% elongation.

Example C10 includes the article of any of examples C1-C15, wherein the SACM is compressible in a range of 20% to 99.9%.

Example C11 includes the article of any of examples C1-C15, wherein the SACM includes an elasticity with a Young's modulus in a range of 30 kPa to 500 kPa.

Example C12 includes the article of any of examples C1-C15, wherein the single hydrogel material comprises a dimethyl acrylamide monomer (DMAm), a sodium alginate block copolymer (P(SA)), and water.

Example C13 includes the article of any of examples C1-C15, wherein the single hydrogel material further comprises N,N'-methylenebisacrylaminde (MBA), N',N',N,N-tetramethlethylenediamine (TMED), calcium sulfate (CA), and ammonium persulfate (APS).

Example C14 includes the article of any of examples C1-C15, wherein the SACM is configured to have the following properties: a speed of sound (SOS) of about 1549 m/s, an attenuation (ATTN) of about 0.14 dB/MHz·cm, an acoustic impedance (Z) of about 1.597 MRayls, a Young's Modulus (E) of about 32 kPa, and an engineering strain ($\varepsilon$) of about −15 mm.

Example C15 includes the article of any of examples C1-C14, wherein the SACM is storable in a sterile or a non-sterile form within a packaging container such that the SACM is ready for use in a clinical imaging application upon removal from the packaging container.

In some embodiments in accordance with the present technology (example C16), an acoustic probe device includes a housing; an array of transducer elements attached to the housing and operable to transmit acoustic signals toward a target volume in a receiving body and received returned acoustic signals that return from at least part of the target volume; and a semi-rigid acoustic coupling medium (SACM) operable to contact and conform to the array of transducer elements at a first end of the SACM and, when the acoustic probe device is engaged with the receiving body, to contact and conform to the receiving body at a second end of the SACM for propagating the transmitted and received returned acoustic signals within the SACM between the array of transducer elements and the receiving body. The SACM includes one or more individual hydrogel materials in a single SACM, where the SACM is structured to have one or more attachment portions located at the first end and an acoustic interface portion spanning away from the one or more attachment portions and terminating at the second end, such that an outward surface of the acoustic interface portion at the second end is structured to (i) be substantially flat, at least at a portion of the outward surface, (ii) have a single curve along one direction of the outward surface, at least at a portion of the outward surface, and/or (iii) have multiple curves in multiple directions along the outward surface, at least at a portion of the outward surface. The outward surface is able to conform to the receiving body for propagation of the acoustic signals into and from the receiving body. The one or more attachment portions are configured to be secured by the acoustic probe device having the array of transducer elements to transmit and receive the propagated acoustic signals.

Example C17 includes the device of example C16, wherein the SACM is capable to conform to both the receiving body and an acoustic probe device having one or more transducer elements without resulting in gaps, creases, or air entrainments in between an external surface of the SACM and the receiving body and the array of transducers.

Example C18 includes the device of any of examples C16-C21, comprising a bracket coupled to the housing to secure the attachment portions of the SACM to the acoustic probe device.

Example C19 includes the device of any of examples C16-C21, wherein the SACM comprises a plurality of the one or more individual hydrogel materials, where the individual hydrogel materials of the plurality couple and conform to each other without resulting in gaps, creases, or air entrainments in between to form a single hydrogel material, the plurality of the individual hydrogel materials each comprising a dimethyl acrylamide monomer (DMAm), a sodium alginate block copolymer (P(SA)), and water.

Example C20 includes the device of any of examples C16-C21, wherein the SACM includes the SACM in any of examples B1 or C1-C15.

Example C21 includes the device of any of examples C16-C20, wherein the device is included in an acoustic imaging system configured to produce a synthetic aperture and/or a tomographic image with high resolution of an anatomical structure of a human or non-human subject based on mechanical and acoustic properties of the SACM.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An acoustic coupling article, comprising:
    a semi-rigid acoustic coupling medium (SACM) operable to contact and conform to an array of transducer elements at a first end of the SACM and to a receiving body at a second end of the SACM to propagate acoustic signals within the SACM between the array of transducer elements and the receiving body,
    wherein the SACM includes a single hydrogel material and is structured to have a shape including one or more attachment portions located at the first end and an acoustic interface portion spanning away from the one or more attachment portions and terminating at the second end, such that an outward surface of the acoustic interface portion at the second end is structured to have multiple curves in multiple directions along the outward surface and is operable to conform to the receiving body to propagate the acoustic signals into and from the receiving body, wherein the attachment portions are configured to be secured by an acoustic probe device having the array of transducer elements to transmit and receive the propagated acoustic signals through the single hydrogel material,
    wherein the single hydrogel material comprises a dimethyl acrylamide monomer (DMAm) as a primary, structural network of the single hydrogel material, a sodium alginate block copolymer (P(SA)) as a secondary, grated sacrificial network of the single hydrogel material, N,N'-methylenebisacrylaminde (MBA), N',N',N,N-tetramethlethylenediamine (TMED), calcium sulfate (CA), ammonium persulfate (APS), and water, such that the SACM is operable to propagate the acoustic signals with the following properties: a speed of sound (SOS) of about 1549 m/s, an attenuation (ATTN) of about 0.14 dB/MHz·cm, an acoustic impedance (Z) of about 1.597 MRayls, a Young's Modulus (E) of about 32 kPa, and an engineering strain ($\varepsilon$) of about -15 mm.

2. The article of claim 1, wherein the SACM is capable to conform to both the receiving body and an acoustic probe device having one or more transducer elements without resulting in gaps, creases, or air entrainments in between an external surface of the SACM and the receiving body and one or more transducers.

3. The article of claim 1, wherein the multiple curves in multiple directions forms a convex surface on at least a portion of the outward surface of the SACM.

4. The article of claim 1, wherein the multiple curves in multiple directions forms a concave surface on at least a portion of the outward surface of the SACM.

5. The article of claim 1, wherein the multiple curves in multiple directions forms a convex surface on at least a first portion of the outward surface and a concave surface on at least a second portion of the outward surface of the SACM.

6. The article of claim 1, wherein the SACM is structured to have a T-shape including two attachment portions located at the first end, and the acoustic interface portion spans away from the two attachment portions and terminates at the second end.

7. The article of claim 1, wherein the SACM is operable to propagate the acoustic signals between the receiving body and the SACM with an acoustic impedance matching of 2 MRayls or less.

8. The article of claim 1, wherein the SACM is operable to propagate the acoustic signals between the receiving body and the SACM with an acoustic attenuation of about 0.001-1.00 dB/cm/MHz.

9. The article of claim 1, wherein the SACM is stretchable in a range of 10% to 1000% elongation.

10. The article of claim 1, wherein the SACM is compressible in a range of 20% to 99.9%.

11. The article of claim 1, wherein the SACM includes an elasticity with a Young's modulus in a range of 30 kPa to 500 kPa.

12. The article of claim 1, wherein the SACM is storable in a sterile or a non-sterile form within a packaging container such that the SACM is ready for use in a clinical imaging application upon removal from the packaging container.

13. The article of claim 1, wherein the SACM is operable to propagate an acoustic composite waveform into a target volume of the receiving body and propagate one or more returned acoustic waveforms received from the target volume, such that a tomographic image of at least part of the target volume is producible by a computer in communication with the array of transducer elements.

* * * * *